(12) United States Patent
Nemoto et al.

(10) Patent No.: US 7,686,789 B2
(45) Date of Patent: Mar. 30, 2010

(54) CHEMICAL LIQUID INJECTION SYSTEM

(75) Inventors: Shigeru Nemoto, Tokyo (JP); Seiichi Ono, Tokyo (JP); Masahiro Sakakibara, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 389 days.

(21) Appl. No.: 11/572,091

(22) PCT Filed: Jul. 14, 2005

(86) PCT No.: PCT/JP2005/012990

§ 371 (c)(1),
(2), (4) Date: Jan. 12, 2007

(87) PCT Pub. No.: WO2006/006643

PCT Pub. Date: Jan. 19, 2006

(65) Prior Publication Data

US 2008/0045901 A1   Feb. 21, 2008

(30) Foreign Application Priority Data

Jul. 14, 2004   (JP) ............................. 2004-207345

(51) Int. Cl.
*A61M 5/00* (2006.01)
*A61M 31/00* (2006.01)
(52) U.S. Cl. ................ 604/246; 604/31; 604/67; 604/131; 604/151; 604/152
(58) Field of Classification Search .................. 604/65, 604/67, 110, 111, 118, 245, 1–5, 7, 131, 604/151
See application file for complete search history.

(56) References Cited

U.S. PATENT DOCUMENTS 5,383,858 A * 1/1995 Reilly et al. ................ 604/152

(Continued)

FOREIGN PATENT DOCUMENTS

EP   1 083 519 A2   3/2001

(Continued)

OTHER PUBLICATIONS

Texas Instruments, "Tag-it—Moving Concepts to Reality." [TIRIS] 2000.*

(Continued)

*Primary Examiner*—Nicholas D Lucchesi
*Assistant Examiner*—Leah Stohr
(74) *Attorney, Agent, or Firm*—Knobbe Martens Olson & Bear, LLP

(57) ABSTRACT

A medical liquid injection system capable of automatically preventing a piston drive mechanism from being driven when a cylinder holding mechanism does not hold a medical liquid syringe properly. When a cylinder member (210) is being held, in a specific direction of rotation about the axis of the mechanism, by a cylinder holding mechanism (120), an RFID chip (230) and an RFID reader (131) become communicable, making the piston drive mechanism operable. On the other hand, when the cylinder member (210) has been rotated by a specified angle from a specific direction, the RFID chip (230) and the RFID reader (131) become incommunicable, not making the piston drive mechanism operable. As a consequence, the piston drive mechanism is not driven when the cylinder holding mechanism (120) is not holding the medical liquid syringe properly.

20 Claims, 14 Drawing Sheets

U.S. PATENT DOCUMENTS

| | | | |
|---|---|---|---|
| 5,868,710 A * | 2/1999 | Battiato et al. | 604/123 |
| 6,019,745 A * | 2/2000 | Gray | 604/131 |
| 6,320,509 B1 | 11/2001 | Brandy et al. | |
| 2002/0038392 A1 | 3/2002 | De La Huerga | |
| 2002/0188259 A1* | 12/2002 | Hickle et al. | 604/189 |
| 2003/0233069 A1 | 12/2003 | Gillespie, Jr. et al. | |
| 2004/0051368 A1 | 3/2004 | Caputo et al. | |

FOREIGN PATENT DOCUMENTS

| | | |
|---|---|---|
| WO | WO 94/25089 A1 | 11/1994 |

OTHER PUBLICATIONS

Supplementary European Search Report dated Aug. 14, 2009 for counterpart European Patent Application No. 05759943.3.

* cited by examiner

Fig.15
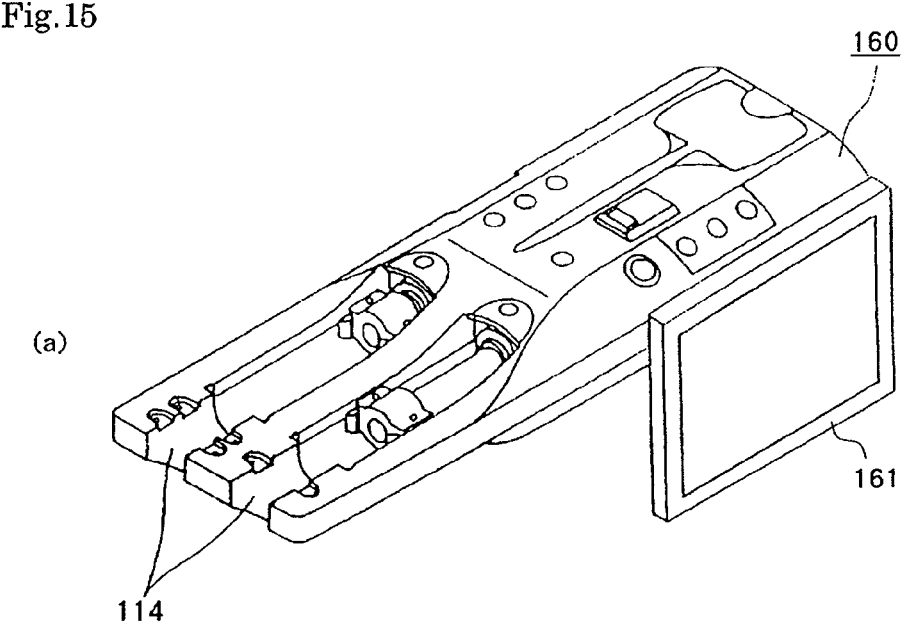
(a)
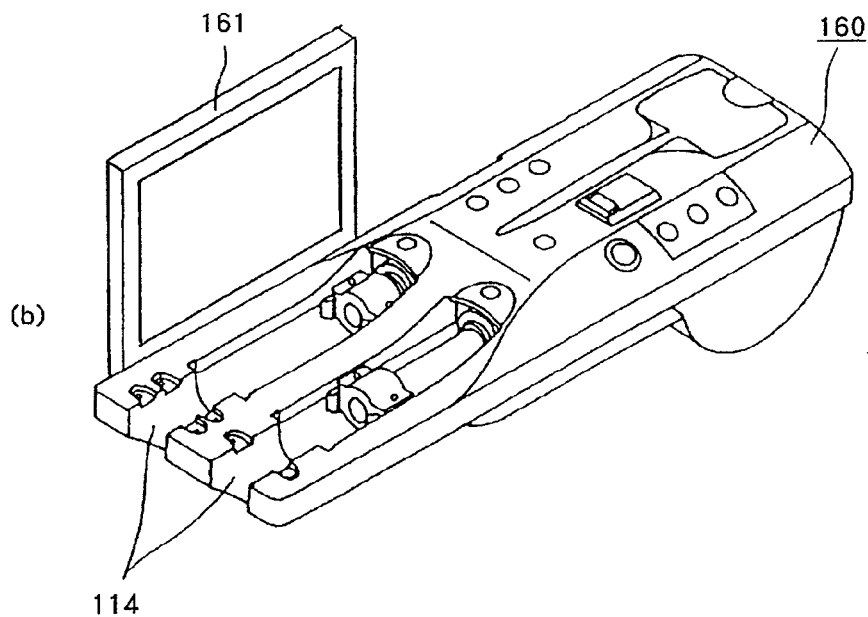
(b)

US 7,686,789 B2

CHEMICAL LIQUID INJECTION SYSTEM

This application is the U.S. National Phase under 35 U.S.C. §371 of International Application PCT/JP2005/012990, filed Jul. 14, 2005, which claims priority to Japanese Patent Application No. 2004-207345, filed Jul. 14, 2004. The International Application was published under PCT Article 21(2) in a language other than English.

TECHNICAL FIELD

The present invention relates generally to a chemical liquid injection system for injecting a liquid in a liquid syringe into a patient with a chemical liquid injector, and more particularly, to a chemical liquid injection system for injecting a contrast medium into a patient whose diagnostic images are taken by an imaging diagnostic apparatus such as a CT (Computed Tomography) scanners.

BACKGROUND ART

Presently available imaging diagnostic apparatuses for capturing diagnostic images of patients include CT scanners, MRI (Magnetic Resonance Imaging) apparatuses, PET (Positron Emission Tomography) apparatuses, ultrasonic diagnostic apparatuses, CT angiography apparatuses, MRA (MR angiography) apparatuses and the like. When the abovementioned imaging diagnostic apparatuses are used, a liquid such as a contrast medium and physiological saline may be injected into a patient. Chemical liquid injectors for automatically performing the injection have been put into practical use.

Such a chemical liquid injector has a piston driving mechanism formed of a driving motor, a slider mechanism and the like, for example. A liquid syringe is removably mounted on the injector. The liquid syringe typically includes a cylinder member and a piston member slidably inserted in the cylinder member.

More specifically, the cylinder member is formed in a cylindrical shape and has a leading end closed and having a conduit formed at the center thereof and a trailing end opened. An annular cylinder flange is formed in the outer circumference of the trailing end, and the piston member is slidably inserted into the cylinder member through the opening at the trailing end.

There are a pre-filled type and a refill type in the liquid syringe. The liquid syringe of the pre-filled type includes a cylinder member filled with a liquid and is wholly sealed by a packing material for shipment. The liquid syringe of the refill type includes a cylinder member which can be filled with a desired liquid by a user.

For simplicity, the following description will be made assuming that the liquid syringe of the pre-filled type is used.

When the liquid in the liquid syringe of the abovementioned type is injected into a patient, an operator prepares for a liquid syringe containing an appropriate liquid and takes out the liquid syringe from the packing material. The operator connects the liquid syringe to a patient through an extension tube and mounts the liquid syringe on a chemical liquid injector. The cylinder flange thereof is held by a cylinder holding mechanism. In this state, the chemical liquid injector presses the piston member into the cylinder member with the piston driving mechanism in accordance with a predetermined operation to inject the liquid into the patient from the liquid syringe.

In that case, the operator determines the rate at which the liquid is injected and the total quantity of the liquid to be injected in view of the type of the liquid and the like, and enters data representing the rate and total quantity into the chemical liquid injector. The chemical liquid injector injects the liquid into the patient based on the entered data. For example, if a contrast medium is injected as the liquid, the image contrast of the patient is changed to allow the imaging diagnostic apparatus to capture a favorable diagnostic image of the patient.

Some chemical liquid injectors can inject physiological saline as well as the contrast medium into the patient. In such a chemical liquid injector, the operator enters as desired an instruction to inject the physiological saline following the completion of the injection of the contrast medium, together with data representing the injection rate and total quantity of the physiological saline, into the chemical liquid injector. Based on the entered data, the chemical liquid injector first injects the contrast medium into the patient and then automatically injects the physiological saline. The subsequently injected physiological saline can push the previously injected contrast medium to reduce the consumption of the contrast medium and also can reduce artifacts in the captured image.

The contrast medium has a high viscosity, but the chemical liquid injector can insert the piston member into the cylinder member of the liquid syringe at high pressure and is preferably used for injection of the contrast medium. To insert the piston member into the cylinder member at high pressure, the cylinder member needs to be held securely.

Thus, a chemical liquid injector invented and practiced by the present applicant includes a pair of metallic flange holding members supported openably or closeably to hold individually the left and the right of a cylinder flange of a liquid syringe put from above (see, for example, non-patent document 1 below).

None-patent document 1: "Dual Shot/A-300 in product guides of Nemoto Kyorindo Co., Ltd" (retrieved on Jun. 30, 2004)

DISCLOSURE OF INVENTION

Technical Problem

In the chemical liquid injectors as described above, the pair of metallic flange holding members can securely hold the cylinder flange of the liquid syringe, so that the piston member can be inserted into the cylinder member of the liquid syringe at high pressure to satisfactorily inject the contrast medium with high viscosity and the like into a patient.

In typical liquid syringes currently used, the cylinder flange has a pair of flat portions in parallel at opposite positions on the annular outer circumference in order to prevent unnecessary rolling and the like. The abovementioned chemical liquid injector is formed to hold the annular portion of the cylinder flange with the flange holding members, and an operator needs to ensure the holding of the annular portion of the cylinder flange with the flange holding members.

If the flange holding members hold the flat portions of the cylinder flange instead of the annular portion, however, the operator may see it as if the liquid syringe was appropriately held in the chemical liquid injector. In this case, since the flange holding members hold the cylinder flange with a smaller area, the cylinder flange may be broken.

In the above-mentioned chemical liquid injector, when the liquid is injected into the patient from the liquid syringe, the operator needs to select the appropriate liquid syringe in order to inject the appropriate liquid. However, some liquid syringes have the same or similar appearances even when they contain different types of liquid, which causes the possibility that the operator mounts the liquid syringe containing an inappropriate liquid on the chemical liquid injector.

In some cases, improperly manufactured liquid syringes may be used, and their inappropriate performance such as low resistance to pressure may cause medical malpractice. The liquid syringe of the pre-filled type should be discarded after it is used once in order to prevent infection and the like. As for the currently available chemical liquid injectors, however, it is impossible to prevent reuse of a liquid syringe after it is used once.

As described above, the operator needs to enter data representing the injection rate and total quantity of the liquid and the like for each of the liquid and the liquid syringe into the Chemical liquid injector. Since the entry operation is complicated and difficult for an unskilled operator, entry of incorrect numerical values cannot be avoided. The currently available contrast media contain active ingredients which differ in concentration severalfold at maximum. If correct numerical values are not entered, the patient may be injected with the contrast medium of the quantity which is several times larger than or a fraction of the appropriate quantity.

The operator needs to enter data representing the injection rate or the like into the chemical liquid injector in some cases based on the area to be imaged and the weight of the patient. The operation is also complicated and erroneous entry cannot be prevented. The present applicant has applied Japanese patent application No. 2002-281109 in which a contrast medium is injected at a variable rate to improve the resulting image contrast, but it is not easy to set the data representing such a variable pattern in the chemical liquid injector.

To solve the above-mentioned problems, the prevent applicant has applied Japanese patent application No. 2003-098058 in which various types of data are recorded on the packing material of a liquid syringe or the like, for example with a bar code, and the bar code is read by the chemical liquid injector to retrieve the recorded data. However, the bar code can represent only a small amount of data, so that only limited data such as identification data can be recorded.

Thus, in the above-mentioned chemical liquid injector, a large amount of data of various types such as the variable pattern is previously registered and retrieved according to the reading of the bar code. However, this requires the previous recording of the various types of data in the chemical liquid injector, and when the recorded data needs to be renewed, the data needs to be updated in the chemical liquid injector.

The present invention has been made in view of the above-mentioned problems, and it is an object thereof to provide a chemical liquid injection system which can automatically prevent driving of a piston driving mechanism while a liquid syringe is not appropriately held by a cylinder holding mechanism.

Technical Solution

The chemical liquid injection system according to the present invention includes a liquid syringe and a chemical liquid injector. The liquid syringe includes a cylinder member and a piston member. In the liquid syringe, the piston member is slidably inserted into the cylinder member from the back, and the cylinder member includes an annular cylinder flange formed on the outer circumference of the trailing end. An RFID (Radio Frequency Identification) chip for wirelessly transmitting recorded data is put on the cylinder member at a predetermined position.

The chemical liquid injector includes a cylinder holding mechanism, a piston driving mechanism, an RFID reader, and an operation control means. The cylinder holding mechanism holds the cylinder member. The piston driving mechanism at least presses the piston member into the held cylinder member. The RFID reader wirelessly received the recorded data from the RFID chip. The operation control means allows operation of the piston driving mechanism only when the recorded data is wirelessly received. The RFID chip can communicate with the RFID reader when the cylinder holding mechanism holds the cylinder member in a particular direction of rotation about the center, and the RFID chip cannot communicate with the RFID reader when the cylinder member is at a position after rotation to a predetermined angle from the particular direction.

Since the RFID reader wirelessly receives the recorded data on the RFID chip when the liquid syringe is appropriately held by the cylinder holding mechanism in the chemical liquid injection system of the present invention, the piston driving mechanism can press the piston member into the cylinder member. However, when the liquid syringe is not appropriately held by the cylinder holding mechanism, the RFID reader does not wirelessly receive the recorded data on the RFID chip, so that the piston driving mechanism cannot press the piston member into the cylinder member.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various components referred to in the present invention do not need to be a separate entity. A plurality of components may be constructed as one member, a single component may be constructed by a plurality of members, a certain component may be part of another component, or a certain component may have a portion overlapping a portion of another component.

Although the directions of forward, rearward, left, right up, and down are specified as shown in the description of the present invention, these directions are defined for convenience to simply describe the relative relationship between components of the present invention and the definition does not limit any direction in manufacture or actual use when the present invention is implemented.

ADVANTAGEOUS EFFECTS

In the chemical liquid injection system of the present invention, the recorded data on the RFID chip can be wirelessly received by the RFID reader only when the liquid syringe is appropriately held by the cylinder holding mechanism, so that the piston driving mechanism can press the piston member into the cylinder member. It is thus possible to automatically prevent insertion of the piston member into the cylinder member when the liquid syringe is not appropriately held.

BRIEF DESCRIPTION OF THE DRAWINGS

FIG. 15 is a perspective view showing the outer appearance of a modification of the present invention.

EXPLANATION OF REFERENCE

100 CHEMICAL LIQUID INJECTOR
116 PISTON DRIVING MECHANISM
120 CYLINDER HOLDING MECHANISM
120 CYLINDER HOLDING MECHANISM
121 FLANGE HOLDING MEMBER
130 RFID READER
131 READER ANTENNA
132 AUXILIARY ANTENNA
140 COMPUTER UNIT SERVING AS VARIOUS MEANS
150 OPERATION CONTROL MEANS
151 CHECK STORING MEANS
152 DATA COMPARING MEANS
153 ALARM OUTPUTTING MEANS
154 DATA ACCUMULATING MEANS
156 DATA HOLDING MEANS
157 DISPLAY CONTROL MEANS
158 INJECTION CONTROL MEANS
200 LIQUID SYRINGE
210 CYLINDER MEMBER
213 CYLINDER FLANGE
220 PISTON MEMBER
230 RFID CHIP
232 CIRCUIT CHIP
233 CHIP ANTENNA
300 CT SCANNER SERVING AS IMAGING DIAGNOSTIC APPARATUS
1000 CHEMICAL LIQUID INJECTION SYSTEM

BEST MODE FOR CARRYING OUT THE INVENTION

Configuration of Embodiment

An embodiment of the present invention will hereinafter be described with reference to FIGS. 1 to 15. As shown in FIGS. 2 to 5, chemical liquid injection system 1000 of the embodiment according to the present invention comprises chemical liquid injector 100, liquid syringe 200, and CT scanner 300 which is an imaging diagnostic apparatus. The system is provided for taking diagnostic images of a patient (not shown) injected with a liquid such as a contrast medium, described later in detail.

Figure 4:
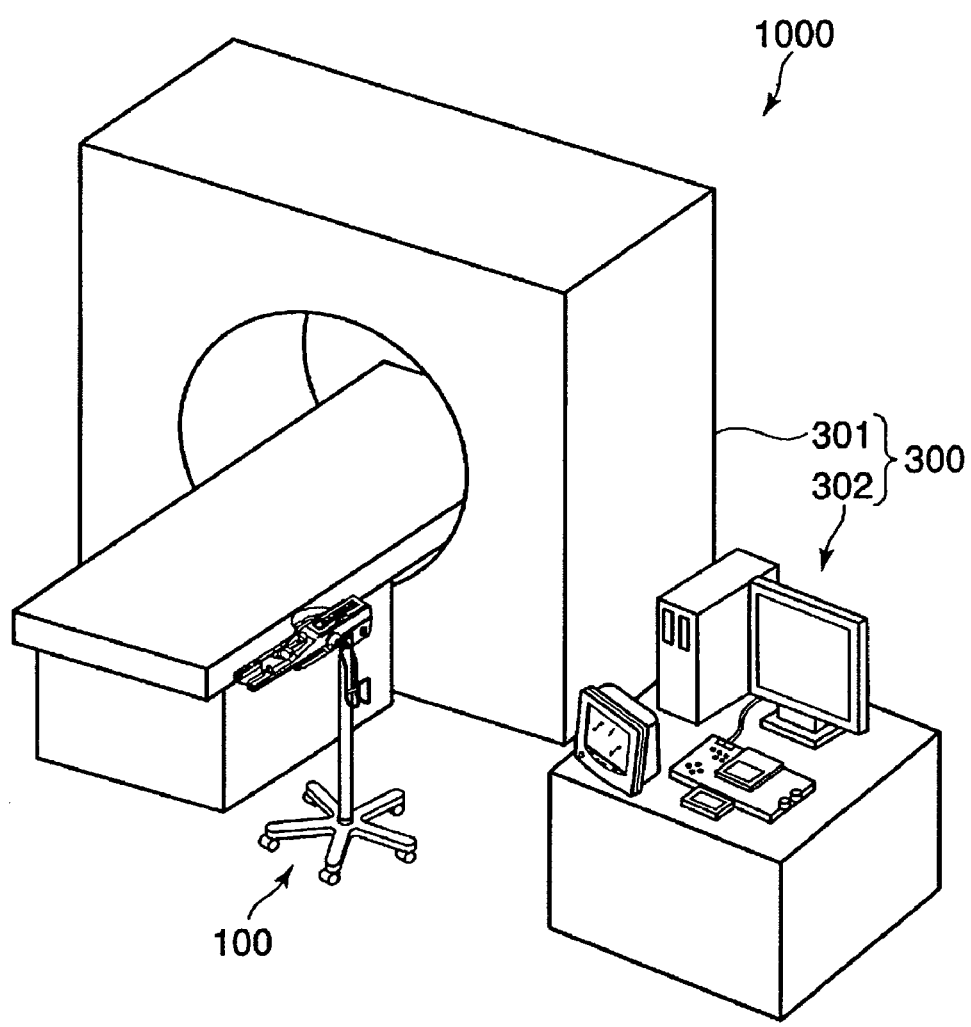
FIG. 4 is a perspective view showing the outer appearance of a CT scanner serving as an imaging diagnostic apparatus.
Figure 5:
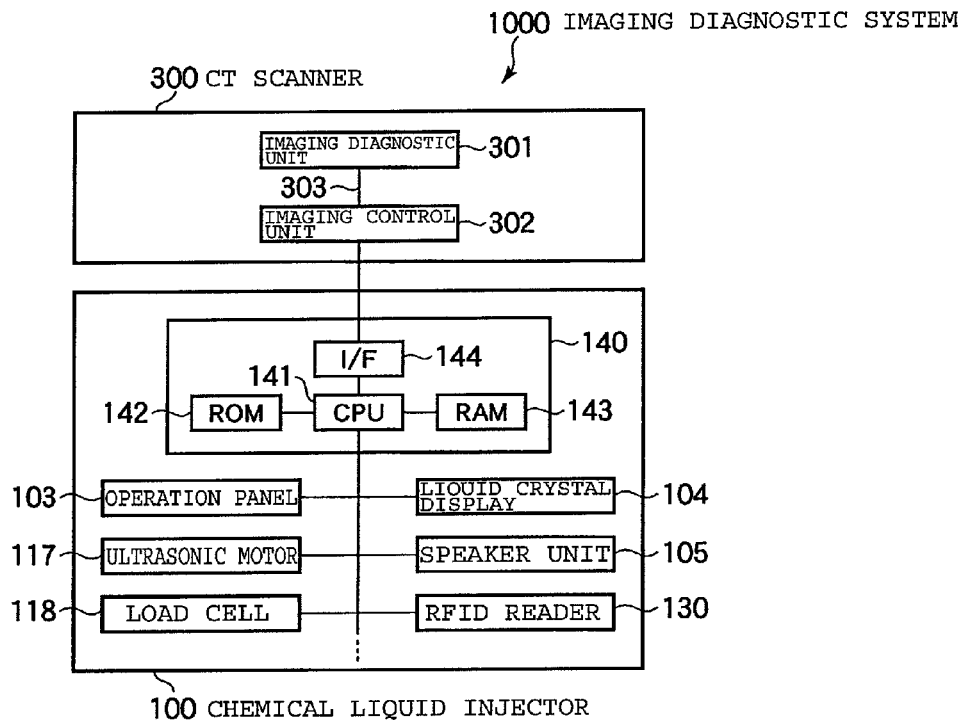
FIG. 5 is a block diagram showing the circuit structure of a chemical liquid injection system.

As shown in FIGS. 4 and 5, CT scanner 300 includes imaging diagnostic unit 301 serving as a mechanism for performing imaging and imaging control unit 302 such that imaging diagnostic unit 301 and imaging control unit 302 are wire-connected through communication network 303. Imaging diagnostic unit 301 shoots a diagnostic image of a patient. Imaging control unit 302 controls the operation of imaging diagnostic unit 301.

Figure 2:
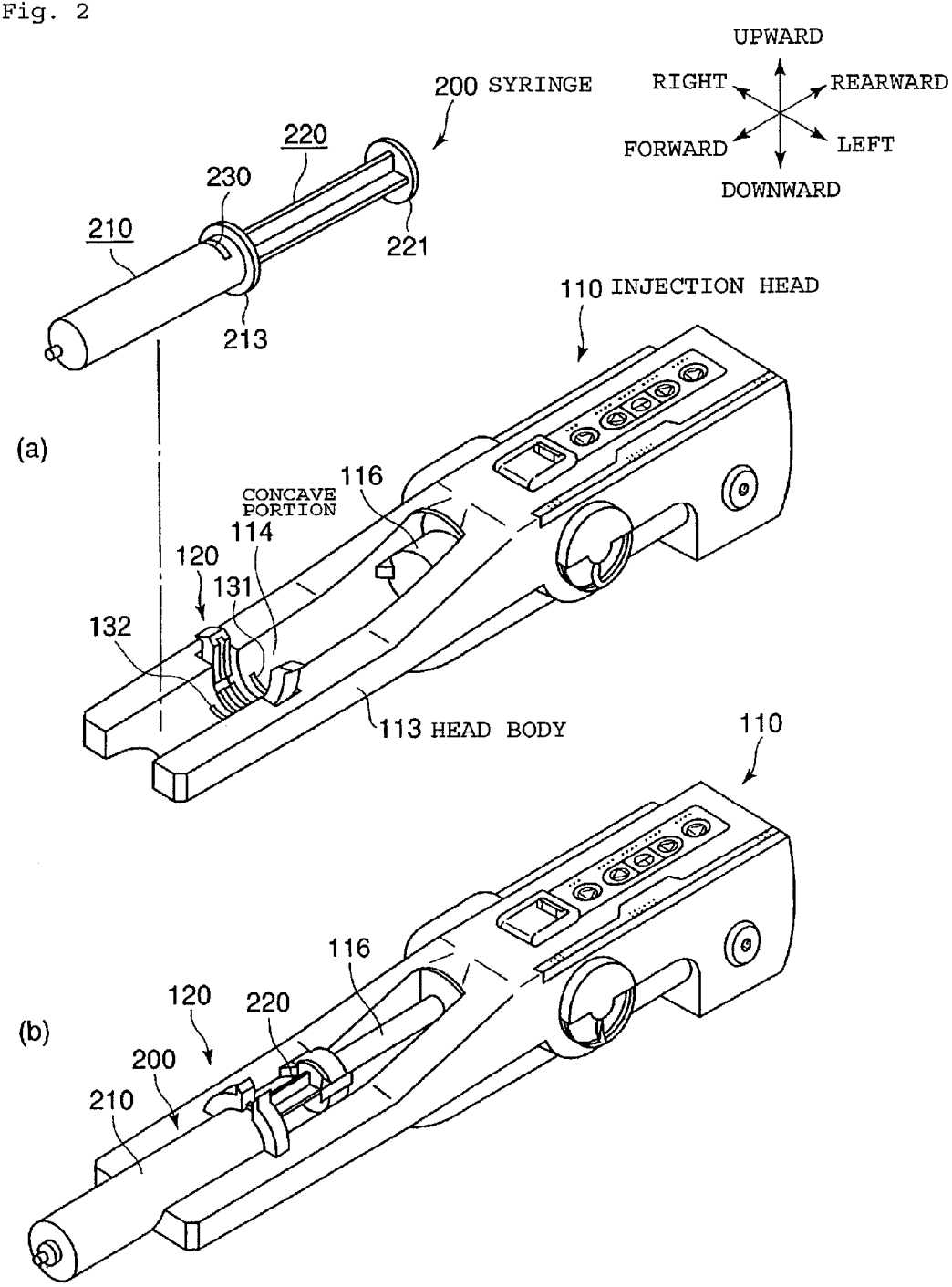
FIG. 2 is a perspective view showing the liquid syringe mounted on an injection head of the chemical liquid injector.
Figure 6:
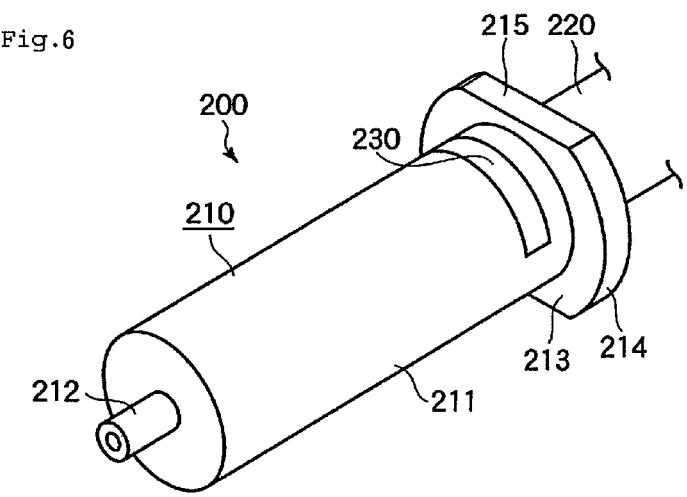
FIG. 6 is a perspective view showing the outer appearance of the liquid syringe.

As shown in FIGS. 2 and 6, liquid syringe 200 comprises cylinder member 210 and piston member 220 wherein piston member 220 is slidably inserted into cylinder member 210. Cylinder member 210 includes cylindrical hollow body 211 which has conduit 212 formed at the closed leading end surface.

The trailing end of body 211 of cylinder member 210 is opened and piston member 220 is inserted from the opening into the interior of body 211. Cylinder member 210 has cylinder flange 213 formed in the outer circumference of the trailing end, and piston member 220 has piston flange 221 formed in the outer circumference of the trailing end.

In chemical liquid injection system 1000 of the embodiment, at least some of liquid syringes 200 to be used are of the pre-filled type. Liquid syringe 200 of the pre-filled type is shipped with cylinder member 210 filled with a liquid. RFID chip 230 is placed on cylinder member 210 of liquid syringe 200. RFID chip 230 has various types of data about liquid syringe 200 recorded thereon such as the name, the identification data indicating the pre-filled type or the refill type, the identification data for each item, the capacity, the resistance to pressure of cylinder member 210, the inner diameter of cylinder member 210, and the stroke of piston member 220.

When liquid syringe 200 of the pre-filled type is used, RFID chip 230 also has various types of data about the contained liquid set thereon such as the name, the ingredients, the viscosity, the expiration date, and the identification data indicating whether the liquid is for CT or MR. When a contrast medium is contained as the liquid in liquid syringe 200 of the pre-filled type, RFID chip 230 also has data set thereon, as required, such as the various pattern with which the injection rate is changed over time.

Figure 7:
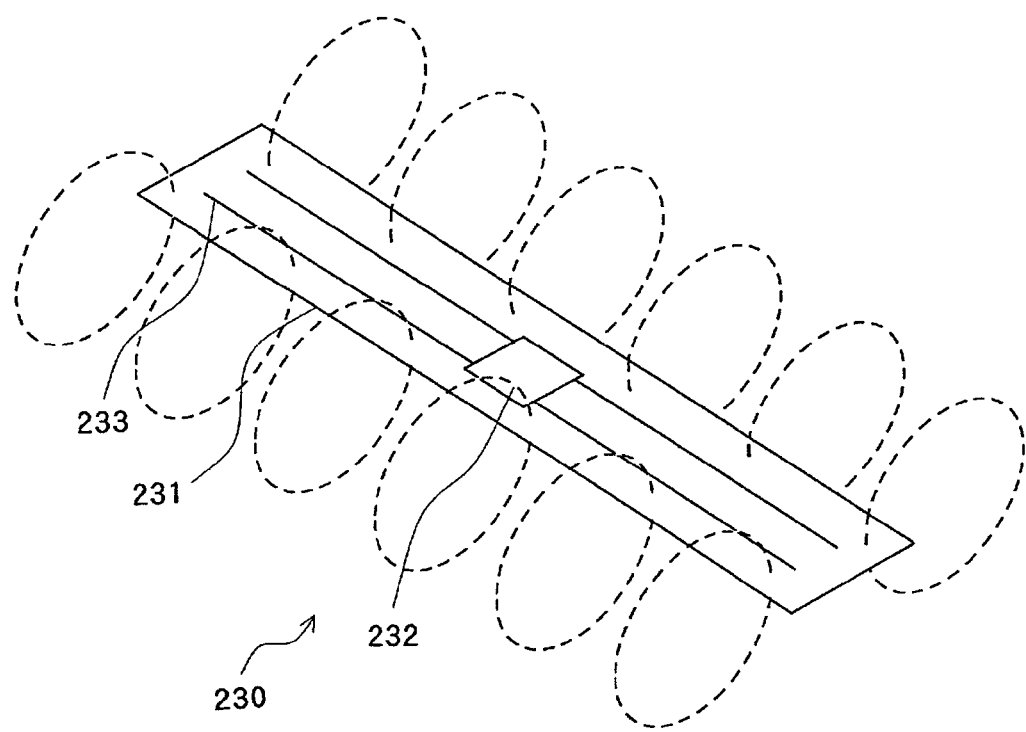
FIG. 7 is a perspective view showing the outer appearance of an RFID chip.

As shown in FIG. 7, RFID chip 230 has chip body 231 formed of an elongated resin sheet and circuit chip 232 included substantially at the center of the sheet. Chip body 231 also has chip antenna 233 formed of printed wiring in a predetermined shape. Circuit chip 232 is mounted on chip antenna 233. For RFID chip 230, a I-chip (registered trademark) with a size of 10×60 (mm) for radio communication at 2.45 (GHz) is preferably used, for example.

Figure 1:
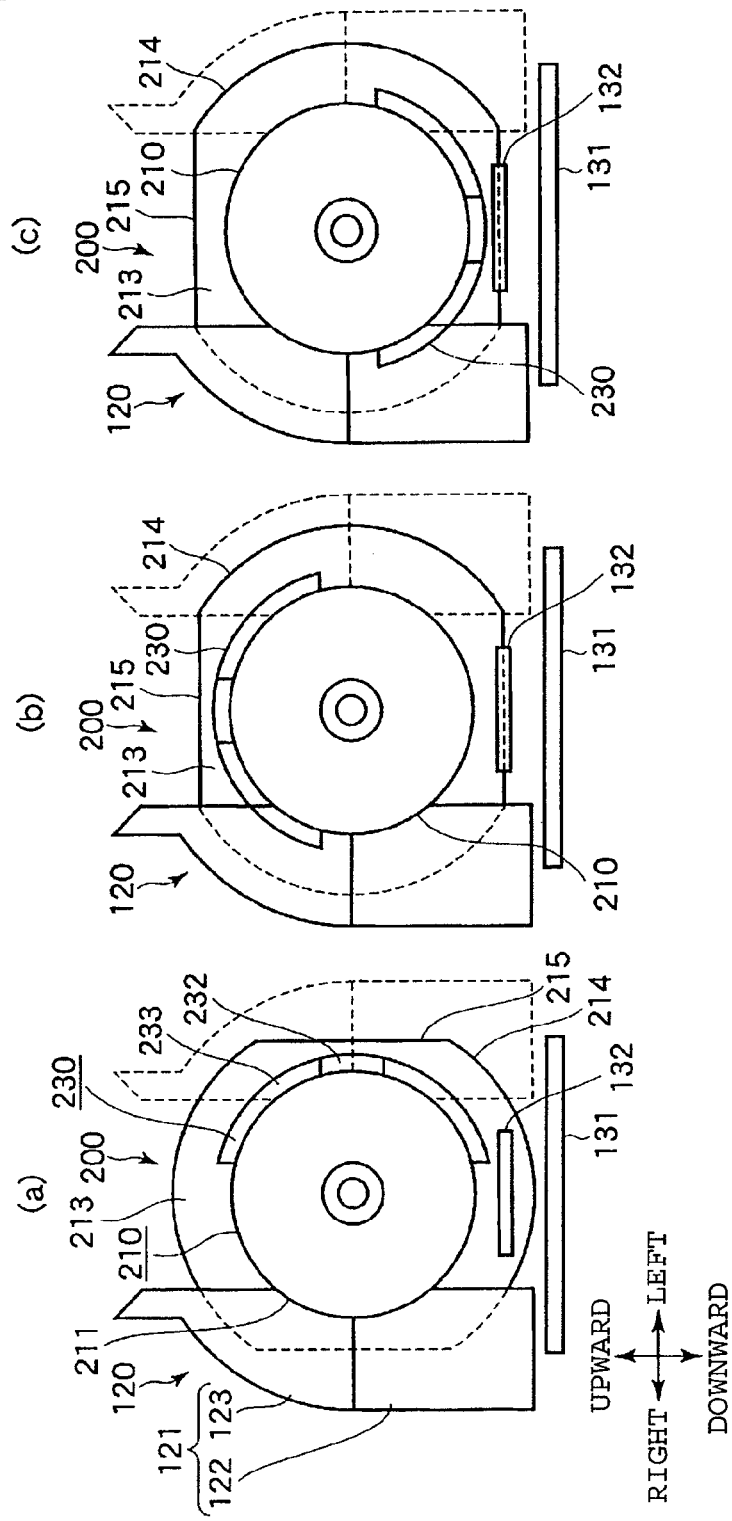
FIG. 1 is a schematic front view showing a liquid syringe mounted on a chemical liquid injector according to an embodiment of the present invention.

As shown in FIGS. 1 and 6, RFID chip 230 is put on liquid syringe 200 close to cylinder flange 213 of cylinder member 210 such that chip antenna 233 is wound on the outer circumference of cylinder member 210. More specifically, liquid syringe 200 includes a pair of flat portions 215 in parallel at opposite positions of annular outer circumference 214 of cylinder flange 213. RFID chip 230 is disposed such that its center is located close to one of paired flat portions 215.

Figure 8:
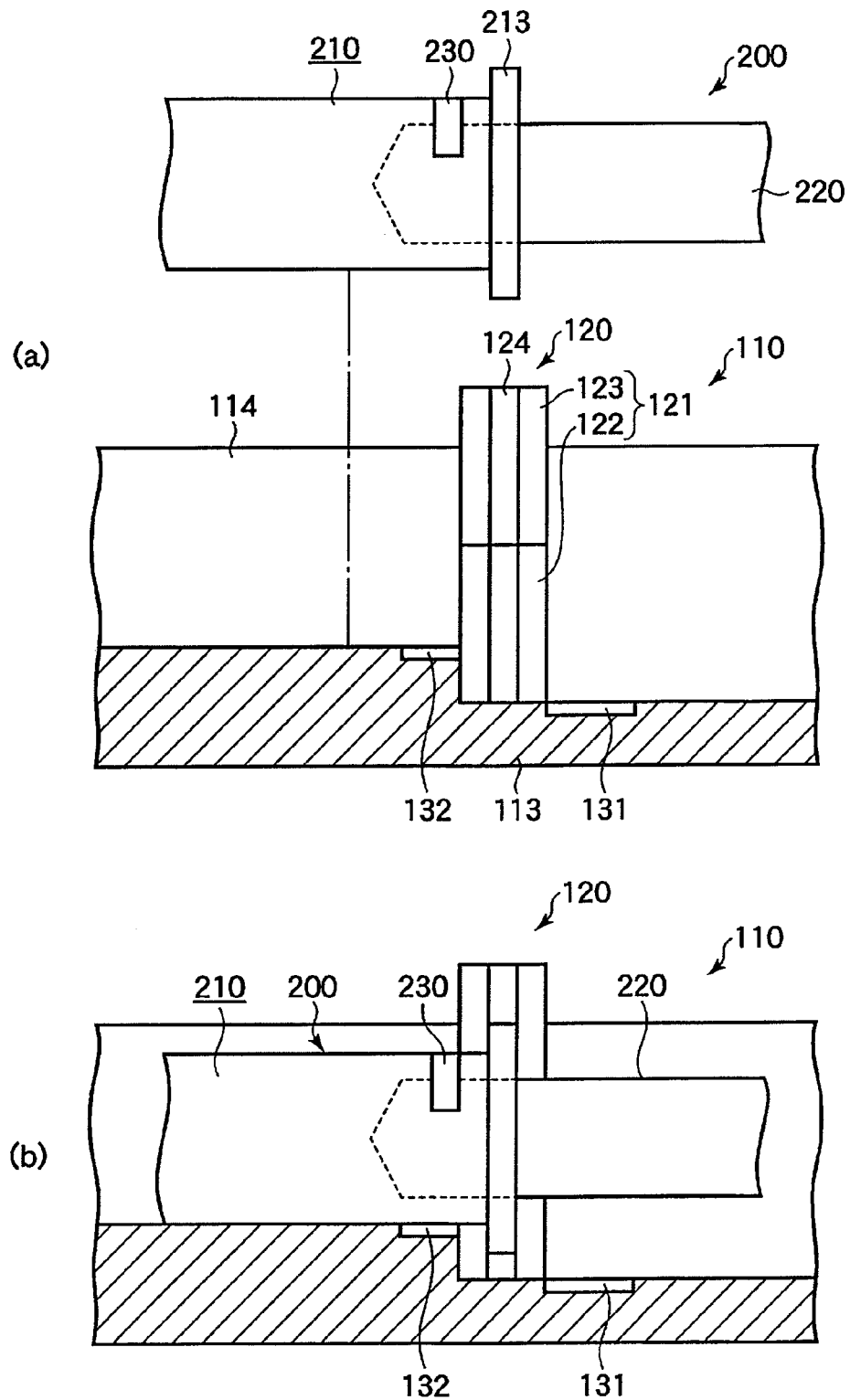
FIG. 8 is a sectional view showing the liquid syringe mounted on the injection head.

The leading end of piston member 220 is placed at the trailing end of cylinder member 210 at least when liquid syringe 200 is mounted on chemical liquid injector 100. As shown in FIG. 8, RFID chip 230 is put on the outer circumference of the trailing end of cylinder member 210 at the position overlapping the leading end of piston member 220.

Figure 3:
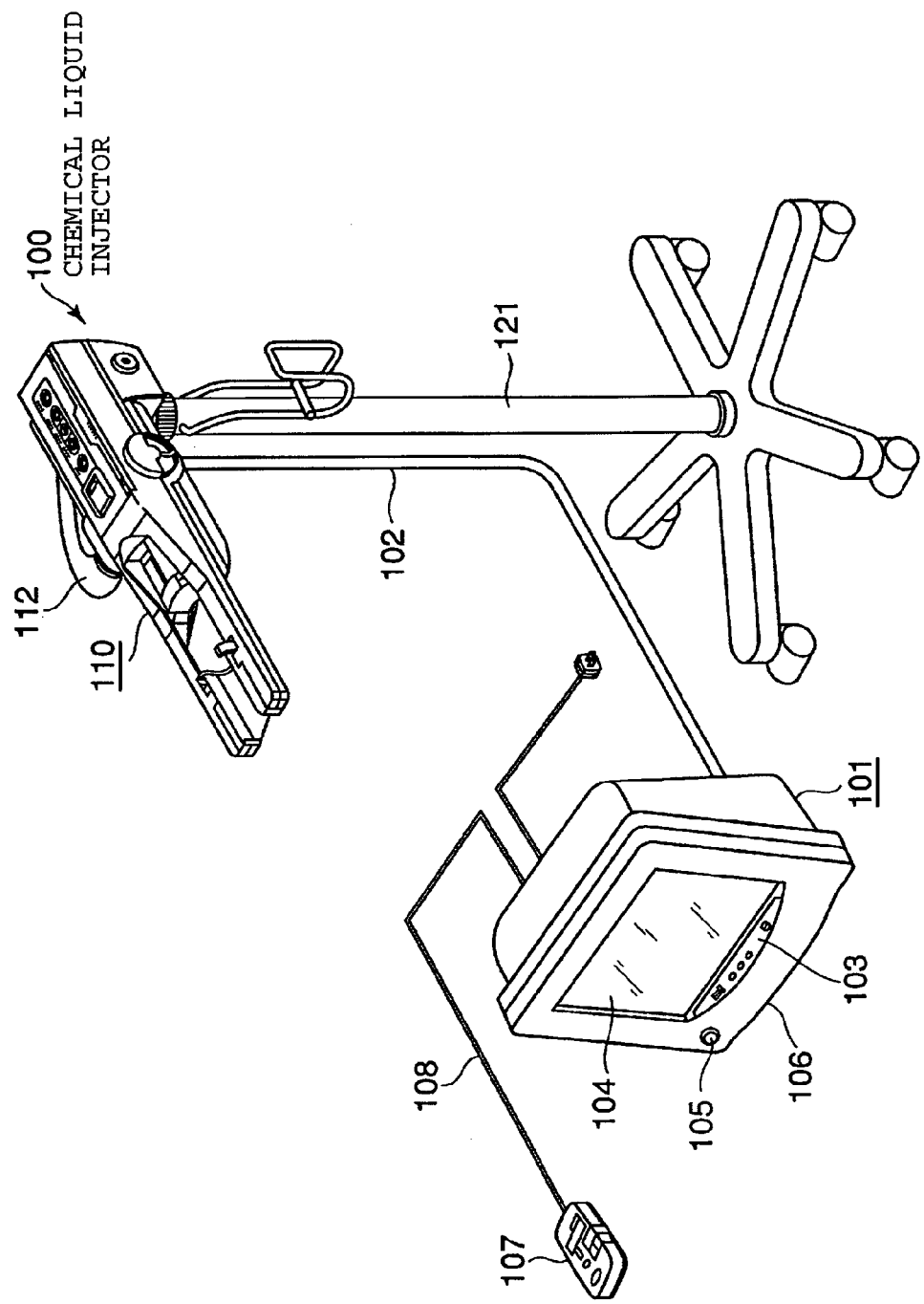
FIG. 3 is a perspective view showing the outer appearance of the chemical liquid injector.

As shown in FIG. 3, chemical liquid injector 100 of the embodiment has injection control unit 101 and injection head 110 constructed as separate components which are wire-connected through communication cable 102. Injection head 110 drives liquid syringe 200 mounted thereon to inject a liquid therefrom into a patient. Injection control unit 101 controls the operation of injection head 110.

Injection head 110 is attached to the top end of caster stand 111 by movable arm 112. As shown in FIG. 2, head body 113 of injection head 110 has concave portion 114 formed as a semi-cylindrical groove in the upper surface for removably mounting liquid syringe 200. Cylinder holding mechanism 120 is formed in the forward section of concave portion 114 for removably holding cylinder flange 211 of liquid syringe 200. Piston driving mechanism 116 is placed in the forward section of concave portion 114 for holding and sliding piston flange 221.

As shown in FIG. 5, piston holding mechanism 116 has ultrasonic motor 117 as a driving source which is free from generation of magnetic field even in operation, and slides piston member 220 through a screw mechanism (not shown) or the like. Load cell 118 is also contained in piston driving mechanism 116 and detects the pressure applied to piston member 220.

Figure 9:
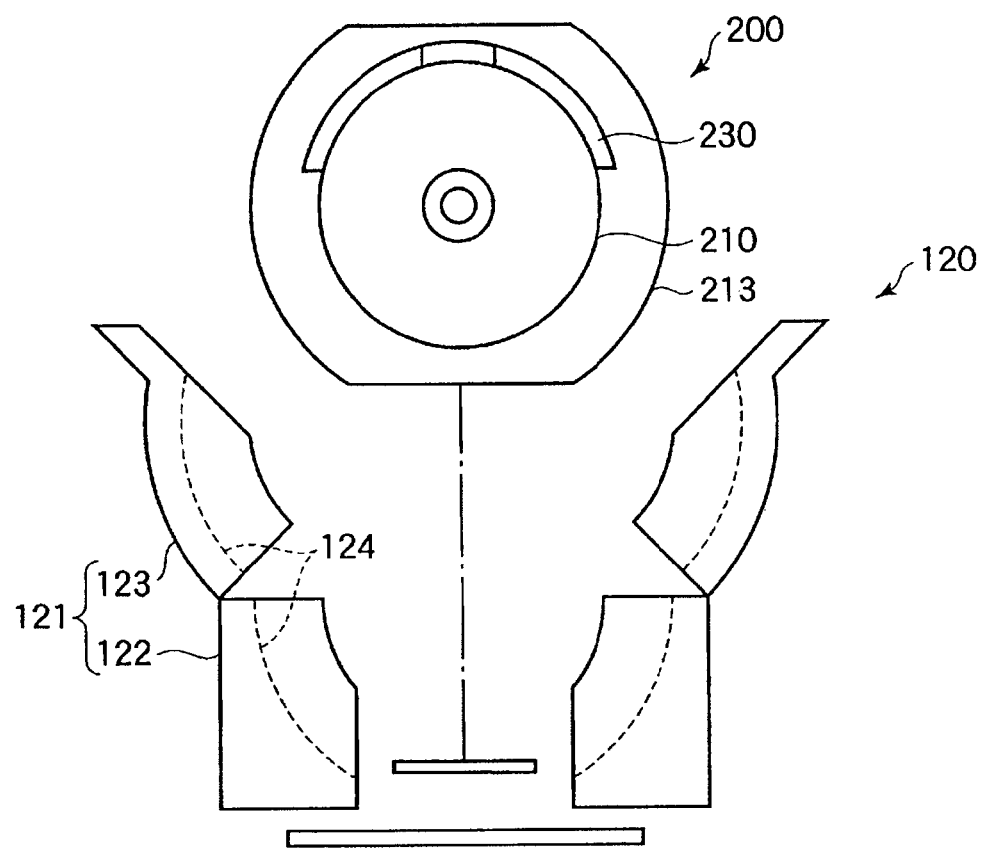
FIG. 9 is a schematic front view showing the liquid syringe mounted on the chemical liquid injector.

As shown in FIGS. 1 and 9, cylinder holding mechanism 120 has a pair of flange holding members 121 on the left and right for holding the left and right of cylinder flange 213 of liquid syringe 200 put from above.

More specifically, flange holding members 121 include fixed holding members 122 and movable holding members 123 which are made of high-strength metal such as stainless alloy. Fixed holding mechanism 122 is fixed to the bottom of concave portion 114 of injection head 110. Movable holding member 123 is pivoted openably or closeably leftward and rightward at the position where it is bonded to fixed holding member 122 from above. Fixed holding member 122 and movable holding member 123 have arc-shaped concave groove 124 in the inner surface. Cylinder flange 213 of liquid syringe 200 is fitted into groove 124.

As shown in FIG. 5, chemical liquid injector 100 of the embodiment has RFID reader 130 which wirelessly communicates with RFID chip 230 of liquid syringe 200. RFID reader 130 has a communication circuit (not shown), reader antenna 131, and auxiliary antenna 132. The communication circuit is contained, for example, in the rearward section of injection head 110.

As shown in FIG. 1, reader antenna 131 is formed of an elongated conductor sheet and is connected to the communication circuit. As shown in FIG. 8, reader antenna 131 is put on the bottom of concave portion 114 at a position at the rear of cylinder holding mechanism 120 and is placed such that its longitudinal direction corresponds to the left-to-right direction.

Auxiliary antenna 132 is formed of an elongated conductor sheet shorter and smaller than reader antenna 131 and is not connected to the communication circuit. Auxiliary antenna 132 is put on the bottom of concave portion 114 at a position in front of cylinder holding mechanism 120 and is disposed such that its longitudinal direction corresponds to the left-to-right direction.

Since chemical liquid injector 100 of the embodiment is formed to have RFID reader 130 and the like added to an existing product, the structure of injection head 110 or the like is not changed from the existing product. Concave portion 114 of injection head 110 has a semicircular shape fitted to cylinder member 210 of liquid syringe 200 in the section in front of cylinder holding mechanism 120, but in the rearward section, the bottom of concave portion 114 is at a lower level in view of assembly of cylinder holding mechanism 120 or the like. Injection head 110 contains a metal frame (not shown) at a position in front of auxiliary antenna 132 in concave portion 114.

As shown in FIG. 5, injection control unit 101 connected to injection head 110 formed as described above through communication cable 102 contains a computer unit 140 and is connected to imaging control unit 302 of CT scanner 300 through communication network 304.

As shown in FIG. 3, injection control unit 101 has operation panel 103, liquid crystal display 104 serving as a data display means, and speaker unit 105, all of which are disposed on the front face of unit housing 106. Injection control unit 101 is wire-connected to controller unit 107 as a separate component through connector 108.

As shown in FIG. 5, in chemical liquid injector 100 of the embodiment, the abovementioned various devices are connected to computer unit 140 which integrates and controls those various devices. Computer unit 140 is formed of a so-called one-chip microcomputer provided with hardware such as CPU (Central Processing Unit) 141, ROM (Read Only Memory) 142, RAM (Random Access Memory) 143, I/F (Interface) 144 and the like. Computer unit 140 has an appropriate computer program installed as firmware or the like in an information storage medium such as ROM 142, and CPU 141 executes various types of processing in accordance with the computer program.

Figure 10:
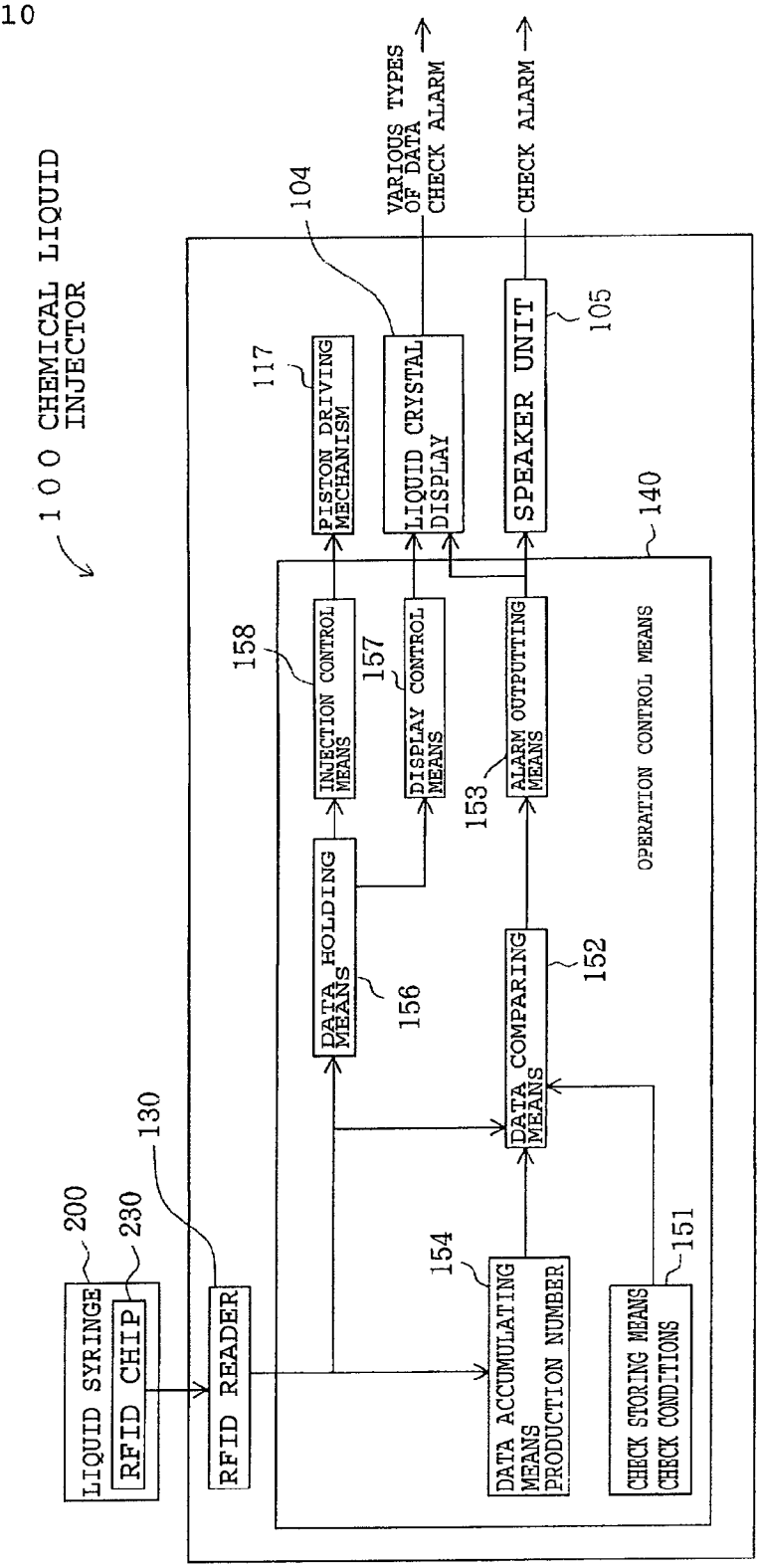
FIG. 10 is a block diagram showing the logical structure of the chemical liquid injector.

In chemical liquid injector 100 of the embodiment, computer unit 140 operates in accordance with the computer program installed as described above to logically have operation control means 150 as shown in FIG. 10. Operation control means 150 logically has various means such as check storing means 151, data comparing means 152, alarm outputting means 153, data accumulating means 154, data holding means 156, display control means 157, and injection control means 158.

Operation control means 150 corresponds to the function of CPU 141 which performs predetermined operations in accordance with the computer program installed in ROM 142 or the like and the various types of data wirelessly received from RFID chip 230. Operation control means 150 has check storing means 151, data comparing means 152, alarm outputting means 153, data accumulating means 154, data holding means 156, display control means 157, and injection control means 158.

Check storing means 151 corresponds to the store area of RAM 143 and the like recognized by CPU 141 and stores predetermined check conditions as data. Data comparing means 152 compares the check conditions stored as data with the various types of data wirelessly received from RFID chip 230. Alarm outputting means 153 outputs and notifies a check alarm in accordance with the comparison result.

More particularly, RAM 143 has data for identifying usable liquid syringe 200 registered thereon in the check conditions. When RFID reader 130 wirelessly receives various types of data from RFID chip 230 of liquid syringe 200, the wirelessly received identification data of liquid syringe 200 is compared with the identification data registered in RAM 143.

When the wirelessly received identification data does not match the registered data, a guidance message, for example "This product not registered as usable device. Check if it is usable" is output as a check alarm with display on liquid crystal display 104 and with sound from speaker unit 105.

The current date and time is constantly updated and held in the check conditions on RAM 143. When the expiration date is wirelessly received from RFID chip 230 of liquid syringe 200, the expiration date is compared with the current date and time. If the current data and time is after the expiration date, a guidance message, for example "Expiration date of this product elapsed. Use new one" is output as a check alarm with display on liquid crystal display 104 and with sound from speaker unit 105.

The production number of each liquid syringe 200 of the pre-filled type is set on RFID chip 230. Data accumulating means 154 stores the data of the production number of liquid syringe 200 of the pre-filled type put on injection head 110 and used to perform injection operation.

Data comparing means 152 compares the stored production number with the production number wirelessly received from RFID chip 230. When the compared production numbers match, alarm outputting means 153 outputs a guidance message, for example "This pre-filled syringe used previously. Use new one" as a check alarm with display on liquid crystal display 104 and with sound from speaker unit 105.

Data holding means 156 holds various types of data wirelessly received from RFID chip 230. Display control means 157 displays the held various types of data on liquid crystal display 104. Injection control means 158 controls the operation of piston driving mechanism 116 based on the held various types of data.

More specifically, RFID chip 230 of liquid syringe 200 has various types of data recorded thereon such as the name, the resistance to pressure, and the capacity of liquid syringe 200 as well as the name, the ingredients, and the expiration date of the liquid in liquid syringe 200. The various types of data are temporarily stored in RAM 143 and output with display on liquid crystal display 104.

When the control data for piston driving mechanism 116 is set on RFID chip 230 of liquid syringe 200, the control data is held in RAM 143 and CPU 141 controls the operation of piston driving mechanism 116 based on the held control data.

For example, when a various pattern for changing the injection rate of the contrast medium over time is recorded as data in RFID chip 230 of liquid syringe 200, CPU 141 changes the operation rate of piston driving mechanism 116 over time in accordance with the variable pattern. When the resistance to pressure is recorded as data on RFID chip 230 of liquid syringe 200, CPU 141 controls the operation of piston driving mechanism 116 such that the resistance to pressure held as data in RAM 143 is not exceeded based on the pressure detected by load cell 118. When the capacity is recorded as data on RFID chip 230 of liquid syringe 200, CPU 141 controls the operation of piston driving mechanism 116 based on the capacity held as data on RAM 143.

Although the abovementioned various means of chemical liquid injector 100 are accomplished by pieces of hardware such as liquid crystal display 104 as required, they are mainly implemented by CPU 141 as a piece of hardware functioning in accordance with the resources and the computer program stored on an information storage medium such as ROM 142.

Such a computer program is stored in an information storage medium such as RAM 143 as software for causing CPU 141 or the like to perform processing operations including the comparison of the check conditions stored as data in RAM 143 and the like with the various types of data wirelessly received from RFID chip 230 when RFID reader 130 wirelessly receives the various types of data from RFID chip 230, the output and notification of the check alarm with data display on liquid crystal display 104 in accordance with the comparison result, the storing of the production number of liquid syringe 200 mounted and used to perform injection operation in RAM 143 or the like, the comparison of the stored production number with the production number wirelessly received as data from RFID chip 230, the output and notification of the check alarm with data display on liquid crystal display 104 in accordance with the comparison result, the holding of the various types of data wirelessly received from RFID chip 230 on RAM 143 or the like, the display of the held various types of data on liquid crystal display 104, and the control of the operation of piston driving mechanism 116 in accordance with the held various types of data.

Operation of the Embodiment

When chemical liquid injection system 1000 of the embodiment is used in the abovementioned structure, injection head 110 of chemical liquid injector 100 is placed near imaging unit 301 of CT scanner 300, and liquid syringe 200 or the like is prepared for use as shown in FIG. 4. An operator opens movable holding members 123 of injection head 110 and puts liquid syringe 200 in concave portion 114 to insert cylinder flange 213 into movable holding members 123 and then closes movable holding members 123.

When liquid syringe 200 is appropriately mounted such that flat portions 215 of cylinder flange 213 are located at the top and bottom as shown in FIGS. 1(*b*) and 1(*c*), RFID chip 230 is located at the top or bottom of liquid syringe 200. The longitudinal direction of chip antenna 233 of RFID chip 230 is substantially in parallel with the longitudinal directions of reader/auxiliary antennas 131, 132 of RFID reader 130, so that RFID chip 230 wirelessly communicates with RFID reader 130.

If liquid syringe 200 is inappropriately mounted such that flat portions 215 of cylinder flange 213 are located on the left and right as shown in FIG. 1(*a*), RFID chip 230 is located on the left or right of liquid syringe 200. Since the longitudinal direction of chip antenna 233 of RFID chip 230 is not in parallel with the longitudinal directions of reader/auxiliary antennas 131, 132 of RFID reader 130, RFID chip 230 does not communicate wirelessly with RFID reader 130.

The underlying principles will be described in brief. RFID chip 230 wirelessly communicates with RFID reader 130 through an electric field (radio communication) and a magnetic field (magnetic coupling), and now attention is focused on the magnetic field to simplify the description. As shown in FIG. 7, chip antenna 233 of RFID chip 230 is formed in an elongated linear shape, so that the magnetic field is produced cylindrically with its longitudinal direction as the center of axis.

Since each of reader/auxiliary antennas 131, 132 of RFID reader 130 is also formed in an elongated linear shape, the magnetic field is produced cylindrically with its longitudinal direction as the center of axis. Thus, chip antenna 233 and reader/auxiliary antennas 131, 132 are favorably coupled magnetically when they are placed in parallel, but when they are not placed in parallel, they are not satisfactorily coupled magnetically.

For this reason, in chemical liquid injection system 1000 of the embodiment, when liquid syringe 200 is appropriately mounted on chemical liquid injector 100 such that flat portions 215 of cylinder flange 213 are located at the top and bottom as shown in FIGS. 1(*b*) and 1(*c*), RFID chip 230 wirelessly communicates with RFID reader 130. However, if liquid syringe 200 is inappropriately mounted on chemical liquid injector 100 such that flat portions 215 of cylinder flange 213 are located on the left and right as shown in FIG. 1(*a*), RFID chip 230 does not wirelessly communicate with RFID reader 130.

The present inventor prototyped liquid syringe 200 having RFID chip 230 put thereon and chemical liquid injector 100 having RFID reader 130 mounted thereon, and rotated liquid syringe 200 mounted on injection head 110 to test the directivity of RFID reader/chip 130, 230.

Figure 11:
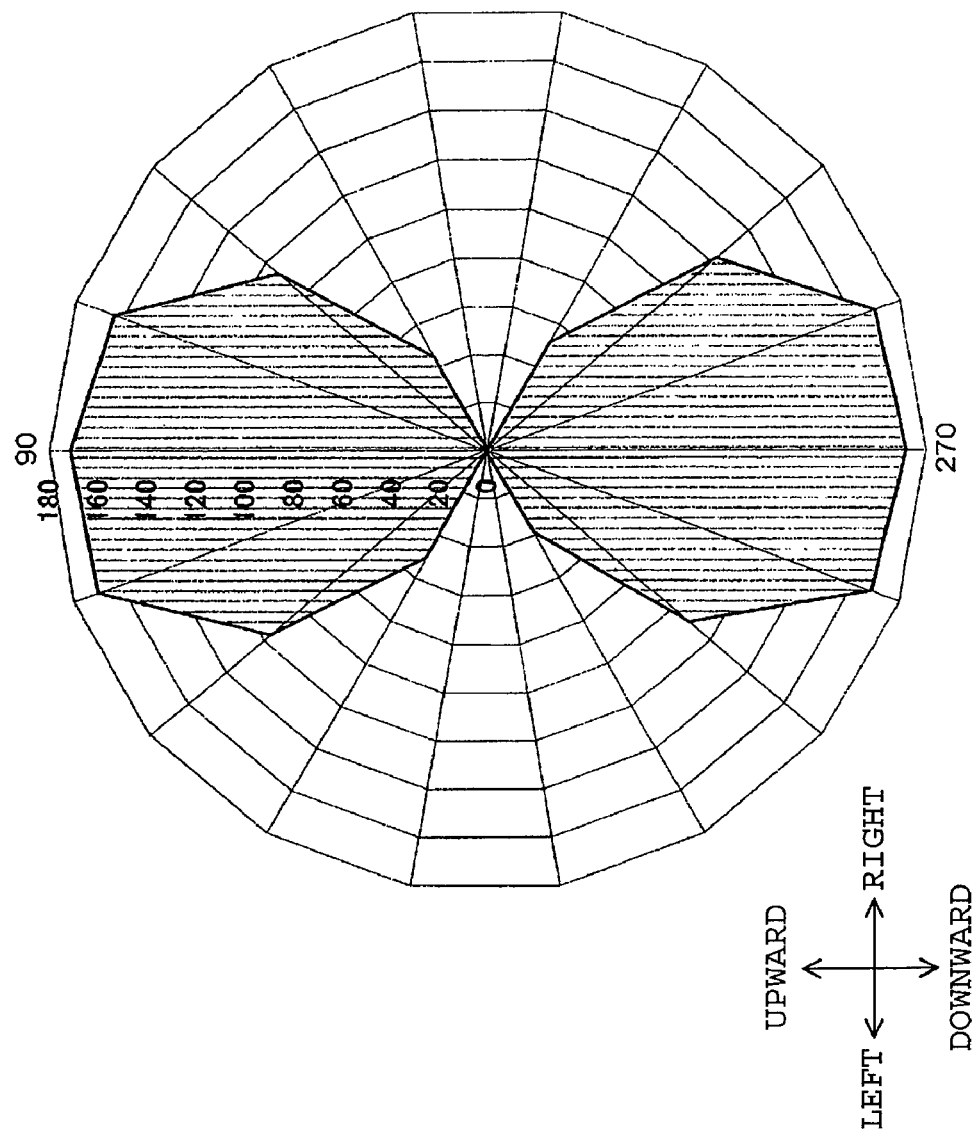
FIG. 11 shows the relationship between the rotation angle of the liquid syringe and the communication sensitivity of the RFID chip/reader.

As shown in FIG. 11, the communication sensitivity of RFID chip 230 and RFID reader 130 was at the maximum when the longitudinal direction of chip antenna 233 is in parallel with the longitudinal directions of reader/auxiliary antennas 131, 132, and was substantially zero when chip antenna 233 is orthogonal to reader/auxiliary antennas 131, 132.

Figure 12:
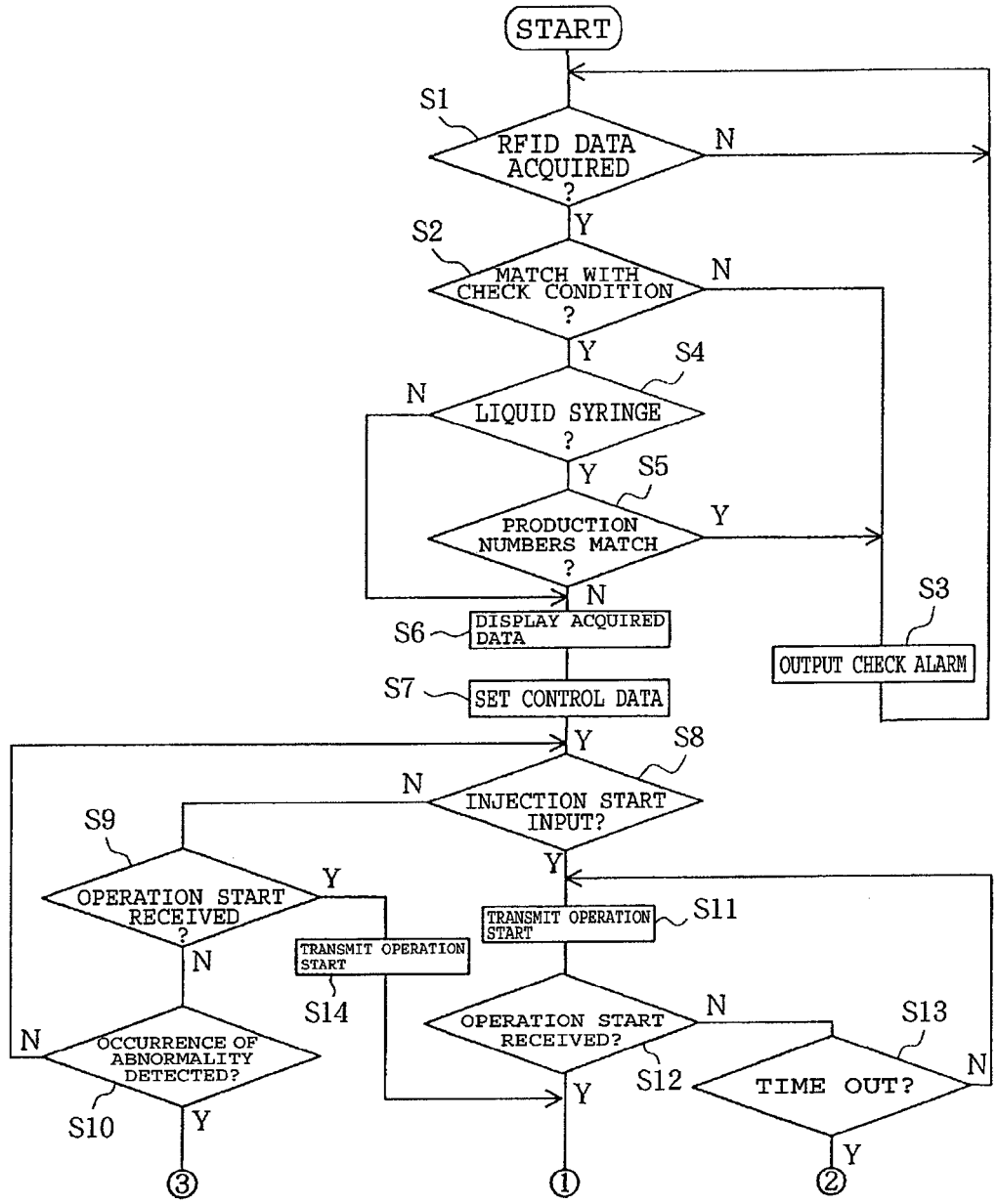
FIG. 12 is a flow chart showing the first half of processing operation of the chemical liquid injector.

Referring to FIG. 12, in chemical liquid injector 100 of the embodiment, when liquid syringe 200 is appropriately mounted on injection head 110 to wirelessly receive various types of data from RFID chip 230 by RFID reader 130 (step S1), computer unit 140 compares the received data with the check conditions registered on RAM 143 (step S2).

Such check conditions include the identification data of usable liquid syringe 200. If the identification data wirelessly received from RFID chip 230 is not included in the check conditions, a guidance message, for example "This product not registered as usable device. Check if is usable" is output as a check alarm with display on liquid crystal display 104 and with sound from speaker unit 105 (step S3).

When liquid syringe 200 is appropriately mounted on injection head 110, RFID chip 230 thereof is naturally faced toward RFID reader 130 with a predetermined interval between them, so that various types of data on RFID chips 230 are wirelessly received by RFID reader 130 (step S1).

The wirelessly received data is also compared with the check conditions (step S2), and a check alarm is output (step S3) if the wirelessly received identification data is not included in the check conditions. Even after the data matches the check conditions, when it is determined that the device to be used is liquid syringe 200 (step S4), the production number wirelessly received from RFID chip 230 is compared with the production number registered in RAM 143 (step S5).

When the compared production numbers match, a guidance message, for example "This syringe used previously. Use new one" is output as a check alarm on liquid crystal display 104 and from speaker unit 105 (step S3).

The various types of data wirelessly received from RFID chip 230 of the appropriate device into chemical liquid injector 100 as described above are output with display on liquid crystal display 104, for example as "Contrast medium syringe (name) made by (manufacturer) mounted. Production number XXX, name of liquid XXX, type of liquid XXX, capacity XXX, resistance to pressure XXX" (step S6).

RFID chip 230 has various types of data to be displayed and various types of data not to be displayed. For example, a binary flag is set in each data to indicate whether or not the data should be displayed. Chemical liquid injector 100 appropriately selects some of the various types of data wirelessly received from RFID chip 230 for display.

When the various types of data wirelessly received from RFID chip 230 of the device into chemical liquid injector 100 include control data such as "resistance to pressure," "capacity," and "variable pattern for changing the injection rate of the contrast medium over time," then the control data is set in RAM 143 of computer unit 140 (step S7). When such control data is not included in the data wirelessly received from RFID chip 230, default control data is set.

As described above, liquid syringe 200 mounted on chemical liquid injector 100 is connected to a patient through an extension tube (not shown) or the like and then the operator makes entry to start operation to operation panel 103. Then, chemical liquid injector 100 detects the entry (step S8) and transmits data for starting operation to CT scanner 300 (step S11).

Figure 14:
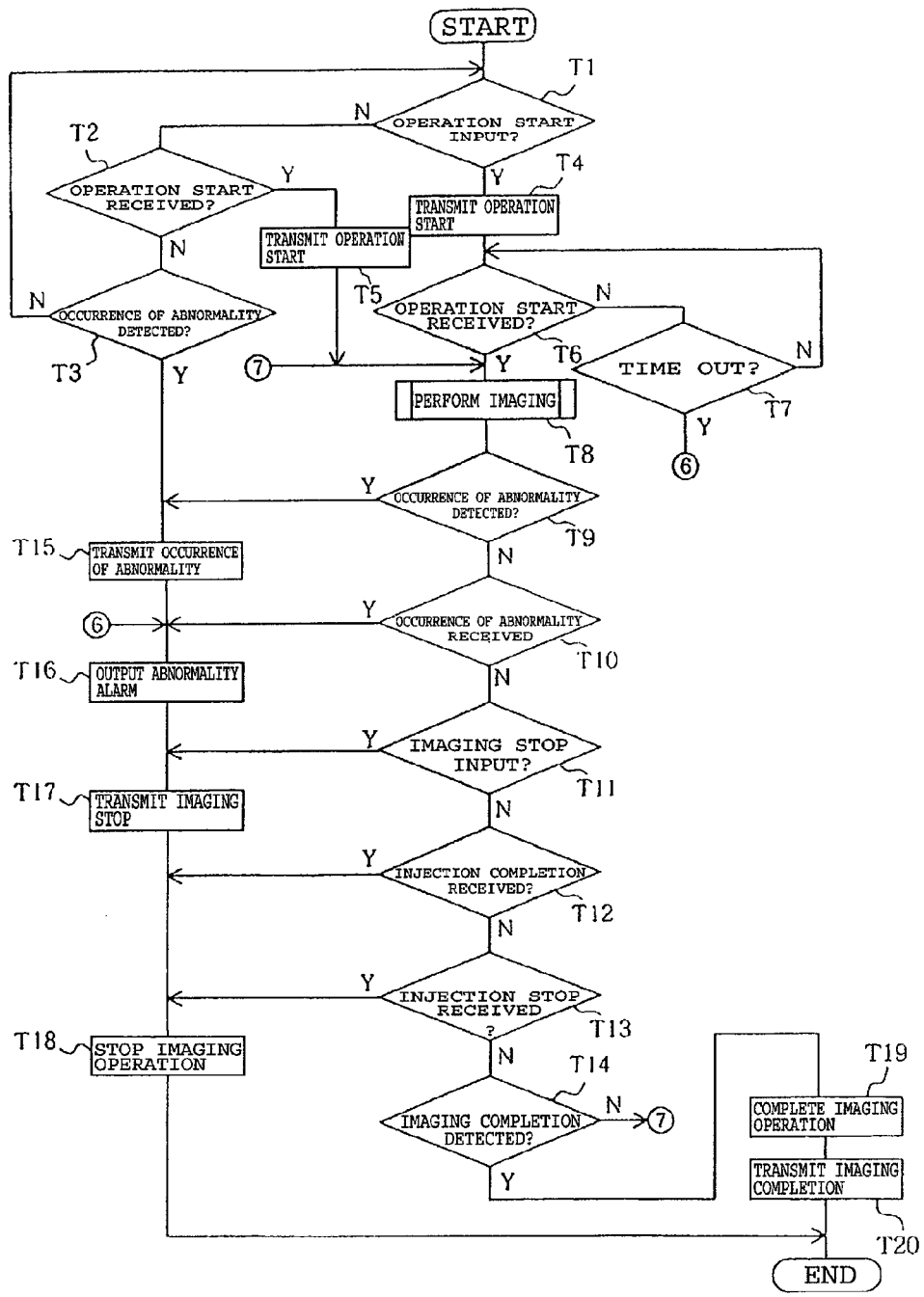
FIG. 14 is a flow chart showing processing operation of the CT scanner.

Referring to FIG. 14, CT scanner 300 receives the data for staring operation from chemical liquid injector 100 (step T2) and transmits the data for starting operation back to chemical liquid injector 100 and performs imaging operation (step T8). Thus, in imaging diagnostic system 1000 of the embodiment, the imaging of CT scanner 300 follows the liquid injection of chemical liquid injector 100.

As shown in FIGS. 12 and 14, in imaging diagnostic system 1000 of the embodiment, when chemical liquid injector 100 is ready as described above (steps S8 to S10) and the operator makes entry to start operation to CT scanner 300 (step T1), the liquid injection of chemical liquid injector 100 follows the imaging of CT scanner 300 (steps T4, T6 and subsequent steps, steps S9, S18 and subsequent steps).

Figure 13:
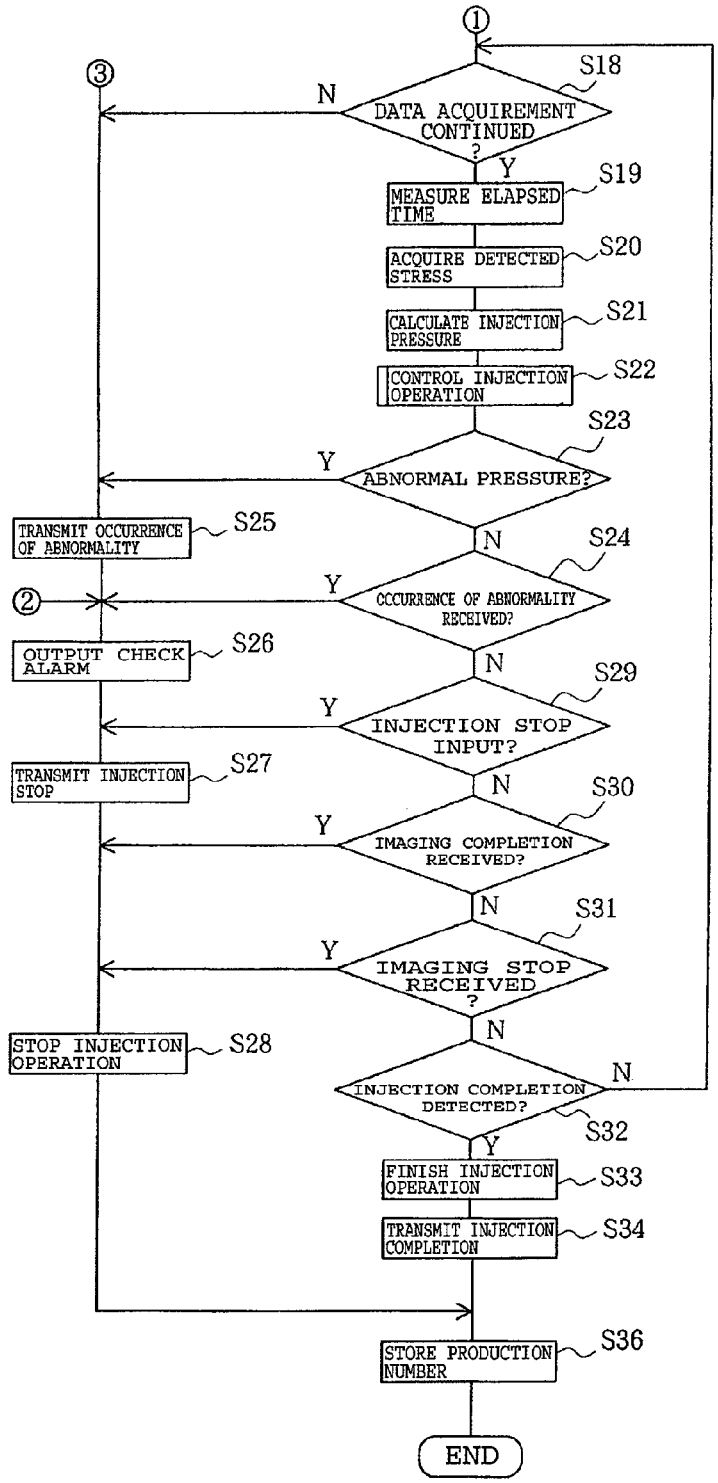
FIG. 13 is a flow chart showing the latter half of the processing operation of the chemical liquid injector.

As shown in FIG. 13, when a series of liquid injection operations is performed (step S18 and subsequent steps) in chemical liquid injector 100 of the embodiment, the elapsed time from the start of the injection is measured (step S19), and the operation of piston driving mechanism 116 is controlled in real time based on the elapsed time and the control data wirelessly received from RFID chip 230 (step S22).

When the variable pattern for changing the injection rate of the contrast medium over time is set in RFID chip 230 of liquid syringe 200, the operation rate of piston driving mechanism 116 is changed over time in accordance with the variable pattern. When piston driving mechanism 116 is driven as described above, the stress detected by load cell 118 is wirelessly received in real time by computer unit 140 (step S20).

The injection pressure of the liquid is calculated from the stress detected by load cell 118 (step S21) based on the viscosity of the liquid, the inner diameter of cylinder member 210 and the like wirelessly received from RFID chip 230. The operation of piston driving mechanism 116 is controlled in real time such that the injection pressure satisfies the pressure range wirelessly received from RFID chip 230 (step S23). Thus, when the resistance to pressure is set on RFID chip 230 of liquid syringe 200, the operation of piston driving mechanism 116 is controlled in accordance with the resistance to pressure.

While liquid syringe 200 is driven by piston driving mechanism 116 as described above, RFID chip 230 is continuously detected by RFID reader 130 (step S18). If the abovementioned detection is stopped before the completion of the injection operation (step S32), the injection operation performed by piston driving mechanism 116 is stopped (step S28).

In addition, a guidance message, for example "Syringe removal detected. Make sure syringe put appropriately" is output as a check alarm with display on liquid crystal display 104 and with sound from speaker unit 105 (step S26). The occurrence of abnormality and the stop of injection are transmitted as data to CT scanner 300 (steps S25 and S28).

Then, CT scanner 300 receives the data representing the occurrence of abnormality (step T10) and outputs the occurrence of abnormality as a check alarm with guidance display or the like (step T16). When it receives the data representing the stop of operation (step T13), the imaging operation is stopped (step S18).

In chemical liquid injector 100 and CT scanner 300 of the embodiment, when the occurrence of abnormality is detected in the abovementioned ready state (steps S10 and T3) or when the occurrence of abnormality is detected during the operation (steps S23 and T9), the occurrence of abnormality is output and notified (steps S26 and T16) and the operation is stopped (steps S28 and T18).

Since the occurrence of abnormality in one of them is transmitted to the other (steps S25 and T15), the other receives the data (steps T10 and S24) and then outputs and notifies the occurrence of abnormality (steps T16 and S26). Since the operation stop in one of them is transmitted to the other (steps S27 and T17), the other receives the data (steps T13 and S31) and stops the operation (steps T18 and S28).

When one of them receives entry to stop operation (steps S29 and T11), the one stops the operation (steps S28 and T18) and transmits it to the other (steps S27 and T17). The other receives the data (steps T13 and S31) and stops the operation (steps T18 and S28).

When the completion of the operation is detected in one of them (steps S32 and T14), the operation is ended (steps S33 and T19) and the end of the operation is transmitted to the other (steps S34 and T20). The other receives the data (steps T12 and S31) and stops the operation (steps T18 and S28).

In chemical liquid injector 100 of the embodiment, when the injection operation is finished normally or abnormally as described above (steps S33 and S28), the identification data wirelessly received from RFID chip 230 of liquid syringe 200 is registered as the check condition in RAM 143 (step S36).

Effect of the Embodiment

In chemical liquid injection system 1000 of the embodiment, RFID chip 230 having the various types of data recorded thereon is placed on liquid syringe 200 as described above. Chemical liquid injector 100 wirelessly receives the various types of data from RFID chip 230 and performs the predetermined operation in accordance with at least some of the various types of data. In this manner, a large amount of data can be easily entered into chemical liquid injector 100 to perform various operations.

In chemical liquid injection system 1000 of the embodiment, only when liquid syringe 200 is appropriately mounted on cylinder holding mechanism 120, RFID chip 230 wirelessly communicates with RFID reader 130. Only when RFID chip 230 wirelessly communicates with RFID reader 130, the operation of piston driving mechanism 116 is permitted. This can automatically prevent insertion of piston member 220 into cylinder member 210 when liquid syringe 200 is not appropriately held.

In chemical liquid injector 100 of the embodiment, computer unit 140 allows piston driving mechanism 116 to operate only when RFID reader 130 detects RFID chip 230. If liquid syringe 200 comes off the appropriate position during the liquid injection, the liquid injection operation can be stopped automatically.

Since the mechanism for detecting the appropriate mounting of liquid syringe 200 is formed of RFID chip/reader 230 and 130 for transmitting the various types of data from liquid syringe 200 to chemical liquid injector 100, the appropriate mounting of liquid syringe 200 can be detected by using the simple structure without requiring a dedicated sensor mechanism.

The wireless communication between RFID chip 230 and RFID reader 130 is inhibited by liquid. As shown in FIG. 8, in liquid syringe 200, the leading end of piston member 220 is located at the trailing end of cylinder member 210, and RFID chip 230 is mounted on the outer circumference of the trailing end of cylinder member 210 at the position overlapping the leading end of piston member 220.

Thus, RFID chip 230 is not placed at a position overlapping the liquid contained in cylinder member 210 in chemical liquid injection system 1000 of the embodiment, so that RFID chip 230 and RFID reader 130 can favorably perform wireless communication without being inhibited by the liquid.

The wireless communication between RFID chip 230 and RFID reader 130 is also inhibited by a metal component. In chemical liquid injector 100, cylinder flange 213 of cylinder member 210 needs to be held by metallic flange holding mechanism 120 to securely hold liquid syringe 200.

In chemical liquid injection system 1000 of the embodiment, however, as shown in FIG. 1, flange holding mechanism 120 individually holds the left and right ends of cylinder flange 213 with the pair of metallic flange holding members 121 on the left and right, and in this state, RFID chip 230 located in the spacing between paired flange holding members 121 wirelessly communicates with RFID reader 130 with reader/auxiliary antennas 131, 132 located below the spacing between paired flange holding members 121.

Thus, in chemical liquid injection system 1000 of the embodiment, even when RFID chip 230 is located at the trailing end of cylinder member 210 to prevent the liquid from inhibiting the wireless communication, metallic flange holding mechanism 120 can securely hold cylinder flange 213 of liquid syringe 200 and also metallic flange holding mechanism 120 does not prevent the wireless communication between RFID chip/reader 230, 130.

In addition, the communication sensitivity between RFID chip 230 and RFID reader 130 is essentially increased as the distance between them is reduced. Actually, the wireless communication cannot be realized favorably when RFID chip 230 is in close contact with RFID reader 130. As described above, since chemical liquid injector 100 of the embodiment basically has the same structure as that of an existing product, so that concave portion 114 in front of flange holding mechanism 121 is formed in the semi-cylindrical shape in close contact with cylinder member 210 of liquid syringe 200 as shown in FIG. 8.

If, for this reason, reader antenna 131 is disposed immediately below RFID chip 230 of liquid syringe 200 held by cylinder holding mechanism 120, RFID chip 230 is in close contact with RFID reader 130 when RFID chip 230 is located at the bottom, which makes it impossible to perform favorable radio communication.

On the other hand, if reader antenna 131 is disposed in front of the abovementioned position, it overlaps the metallic frame contained in injection head 110 to prevent favorable radio communication between RFID chip 230 and RFID reader 130. If only reader antenna 131 is disposed at the back of cylinder holding mechanism 120, RFID chip 230 is at a large distance from RFID reader 130 when RFID chip 230 is disposed at the top since the bottom of concave portion 114 is located at the lower level in that position, thereby inhibiting satisfactory radio communication.

In chemical liquid injector 100 of the embodiment, however, reader antenna 131 is placed at the back of cylinder holding mechanism 120 and auxiliary antenna 132 is disposed immediately below RFID chip 230 of liquid syringe 200 held by cylinder holding mechanism 120.

Thus, if RFID chip 230 is located at the top, RFID reader 130 can perform favorable wireless communication with RFID chip 230 through auxiliary antenna 132 by reader antenna 131. On the other hand, if RFID chip is located at the bottom, RFID chip 230 is not in close contact with RFID reader 130. RFID reader 130 can achieve favorable wireless communication with RFID chip 230 in close contact with auxiliary antenna 132 by reader antenna 131.

The present inventor has found that the wireless communication between RFID chip/reader 230, 130 is prevented by a conductor longer and larger than reader/chip antennas 131, 233, but a conductor shorter and smaller than reader/chip antennas 131, 233 does not prevent the wireless communication between RFID chip/reader 230, 130 and can favorably relay the communication. Thus, auxiliary antenna 132 is formed to have a shorter and smaller size than reader/chip antennas 131, 233 and favorably relays the wireless communication between reader/chip antennas 131, 233.

Further, in chemical liquid injection system 1000 of the embodiment, at least some of the various types of data wirelessly received from RFID chip 230 are held as data and output with display on liquid crystal display 104, so that the operator can check the various types of data of liquid syringe 200 and the like easily and reliably.

Chemical liquid injector 100 of the embodiment compares the check conditions stored as data with the various types of data wirelessly received from RFID chip 230, and as required, outputs the check alarm. For example, when the operator attempts to use liquid syringe 200 which is not allowed in chemical liquid injector 100 or liquid syringe 200 with the expiration date elapsed, the check alarm can be output to prevent any medical malpractice reliably.

Particularly, in chemical liquid injector 100 of the embodiment, when the data is read from RFID chip 230 of liquid syringe 200, the production number of each item is stored. If the production number newly received wirelessly from RFID chip 230 is already stored, the check alarm is output. It is thus possible to readily and reliably prevent medical malpractice such as repeated use of liquid syringe 200 which should be discarded after it is used once.

In chemical liquid injection system 1000 of the embodiment, when the variable pattern for changing the injection rate of the constant medium over time is recorded on RFID chip 230 of liquid syringe 200 of the pre-filled type filled with the contrast medium, chemical liquid injector 100 changes the injection rate of the contrast medium over time in accordance with the variable pattern.

Consequently, the optimal image contrast can be maintained favorably, and the minimum amount of the injected contrast medium can be used to reduce physical burdens on the patient. In addition, it is not necessary to previously register the data of the complicated variable pattern in chemical liquid injector 100. For example, a new variable pattern for a new contrast medium can be simply input as data to chemical liquid injector 100 from RFID chip 230 of liquid syringe 200.

In chemical liquid injector 100 of the embodiment, the pressure of the injected liquid is detected from the stress on piston member 220 of liquid syringe 200, and if the injection pressure reaches an abnormal value, the check alarm is output and the injection operation is forcedly stopped. This can prevent medical malpractice of injection of the liquid at an abnormal pressure.

The detection of the pressure of the liquid by chemical liquid injector 100 as described above requires not only the stress on piston member 220 of liquid syringe 200 but also the various types of data such as the inner diameter of cylinder member 210 and the viscosity of the liquid. The various types of data are input to chemical liquid injector 100 from RFID chip 230. Thus, in chemical liquid injection system 1000 of the embodiment, chemical liquid injector 100 can appropriately detect the injection pressure of each liquid of liquid syringe 200 without requiring complicated operations of manual entry of the various types of data into chemical liquid injector 100 by the operator.

In imaging diagnostic system 1000 of the embodiment, since the liquid injection in chemical liquid injector 100 is automatically associated with the imaging in CT scanner 300, the diagnostic images can be taken in an appropriate timing from the patient injected with the contrast medium in an appropriate timing.

Modifications of the Embodiment

The present invention is not in any way limited to the abovementioned embodiment, but various changes and modifications may be made therein without departing from the scope of the invention. For example, in the above embodiment, only one liquid syringe 200 is mounted on one concave portion 114 of injection head 110 in chemical liquid injector 100. As shown in FIG. 15, it is possible to provide a chemical liquid injector (not shown) in which a plurality of liquid syringes 200 are individually mounted on a plurality of concave portions 114 of injection head 160.

In this case, RFID reader 130 can be provided for each of the plurality of concave portions 114 of injection head 160, and recorded data can be detected from each of RFID chips 230 of the plurality of liquid syringes 200. RFID readers 130 can detect data on the plurality of RFID chips 230 on a time-division basis, and for example, one communication circuit can be provided for RFID readers 130 and a plurality of reader antennas 131 can be placed individually in the plurality of concave portions 114.

In the above embodiment, the recorded data detected by RFID reader 130 from RFID chip 230 is output with display on liquid crystal display 104 of injection control unit 101 separate from injection head 110. However, as shown in FIG. 15, display panel 161 may be mounted on injection head 160 and recorded data on RFID chip 230 may be output on display panel 161.

In this case, immediately after liquid syringe 200 is appropriately mounted in injection head 160, recorded data is output with display on display panel 161 of injection head 160. This allows immediate check of appropriate mounting of liquid syringe 200 and intuitive recognition of the displayed data.

In the above embodiment, since the existing product is used as chemical liquid injector 100, reader/auxiliary antennas 131, 132 are individually disposed on injection head 110 as shown in FIG. 8. However, it is possible to form a hole portion (not shown) at the position of auxiliary antenna 131 in concave portion 114 of injection head 110 to place only reader antenna 131 at the bottom of the hole portion.

In the above embodiment, to use liquid syringe 200 or the like only once, the data of the production number of each liquid syringe 200 is wirelessly received from RFID chip 230 of liquid syringe 200 by RFID reader 130 and stored in chemical liquid injector 100, and if a newly wirelessly received production number is already stored, the check alarm is output.

Alternatively, it is possible that a rewritable product is used as RFID chip 230 of liquid syringe 200, chemical liquid injector 100 records the "used" or the fact that liquid syringe 200 has been mounted and the liquid thereof has been injected on RFID chip 230 of liquid syringe 200, and a check alarm is output when the data "used" is wirelessly received from RFID chip 230 of newly mounted liquid syringe 200.

Since a large number of production numbers do not need to be stored in chemical liquid injector 100 in this case, an overflow or the like of RAM 143 can be prevented, and RAM 143 having a large capacity does not need to be included uselessly. In addition, even when the data stored in chemical liquid injector 100 is reset erroneously, inappropriately repeated use of liquid syringe 200 or the like can be prevented.

In the above embodiment, the control data for the liquid injection is wirelessly received from RFID chip 230 of liquid syringe 200 and the like into chemical liquid injector 100, and chemical liquid injector 100 controls the operation of the liquid injection based on the control data. It is also possible that chemical liquid injector 100 controls the operation of the liquid injection based on a combination of control data wirelessly received from RFID chip 230 of liquid syringe 200 and control data entered through operation panel 103 or the like.

For example, it is possible that the variable pattern of liquid injection over time is recorded on RFID chip 230 of liquid syringe 200 as described above, and when an operator enters the data of an area to be imaged by CT scanner 300 through operation panel 103 or the like, the variable pattern is adjusted in accordance with the area to be imaged.

In the above embodiment, chemical liquid injector 100 finishes the injection operation and registers the production number wirelessly received from RFID chip 230 of liquid syringe 200, and then ends the various types of operations. Alternatively, for example, it is possible that when chemical liquid injector 100 finishes the injection operation and registration of the production number as described above and detects removal of liquid syringe 200 with RFID reader 130, chemical liquid injector 100 automatically moves piston driving mechanism 116 backward to the initial position at the backend.

It is also possible that when chemical liquid injector 100 completes the various types of operations and moves piston driving mechanism 116 back to the initial position and then detects the mounting of new liquid syringe 200 with RFID reader 130, chemical liquid injector 100 automatically moves piston driving mechanism 116 forward to the standby position for holding piston members 210. In this case, liquid syringe 200 can be removed and put in chemical liquid injector 100 in an appropriate timing to place piston driving mechanism 116 automatically to the appropriate position, so that any special operation is not required to place piston driving mechanism 116 and the convenience can be improved.

In the above embodiment, the various types of data are recorded by the manufacturer on RFID chip 230 of liquid syringe 200. Alternatively, the various types of data may be recorded on RFID chip 230 of liquid syringe 200 or the like in a medical facility such as a hospital where liquid syringe 200 is used.

In this case, desired data can be provided for liquid syringe 200 in the medial facility. For example when a desired liquid is filled into liquid syringe 200 of the refill type, various types of data of the liquid can be recorded on RFID chip 230. In such a case, however, it is preferable that the production number is previously recorded on RFID chip 230 to prevent repeated use of liquid syringe 200 as described above.

In the above embodiment, a product for wireless communication with microwaves at 2.45 (GHz) is intended as RFID chip 230. For example, a product for wireless communication with UHF waves at 900 (MHz) may be used as RFID chip 230 (not shown). Such an RFID chip and a reader antenna therefor may be formed in a predetermined plane shape such as a square and a circle rather than an elongated shape. In this case, the orientation of the liquid syringe is detected by determining whether or not the plane directions of the chip antenna and reader antenna are substantially in parallel with each other, not the longitudinal directions.

In the above embodiment, CT scanner 300 is used as the imaging diagnostic apparatus and chemical liquid injector 100 injects the contrast medium for CT. For example, an MRI apparatus or a PET apparatus may be used as the imaging diagnostic apparatus and the chemical liquid injector may inject a contrast medium therefor.

In the above embodiment, the respective portions of chemical liquid injector 100 have been specifically described, but the portions may be changed in various manners. For example, the driving source of the piston driving mechanism may be realized by a DC (Direct Current) motor or an AC (Alternating Current) motor, or the display panel may be realized by an organic EL (Electro-Luminescence) display or a plasma display (not shown).

In the above embodiment, CPU 141 operates in accordance with the computer program stored in RAM 143 or the like to realize logically various means as various functions of chemical liquid injector 100. Each of the various means may be formed as specific hardware, or some of them may be stored as software on ROM 143, while others may be formed as hardware.

The invention claimed is:

1. A chemical liquid injection system at least comprising: a liquid syringe including a cylindrical cylinder member and a piston member slidably inserted into the cylinder member from the back thereof the cylinder member including an annular cylinder flange formed on an outer circumference of a trailing end; and a chemical liquid injector for injecting the liquid into a patient by relatively moving the cylinder member and the piston member of the liquid syringe, wherein the liquid syringe has an RFID chip put on a predetermined position of the cylinder member for wirelessly transmitting recorded data, the chemical liquid injector includes a cylinder holding mechanism for holding the cylinder member, a piston driving mechanism for at least pressing the piston member into the held cylinder member, an RFID reader for wirelessly receiving the recorded data from the RFID chip, and a computer unit configured to allow operation of the piston driving mechanism only when the recorded data is wirelessly received, wherein the RFID reader continuously detects the RFID chip during injection, and if said detection is interrupted, injection operation by the piston driving mechanism is stopped, and the RFID chip can communicate with the RFID reader when the cylinder holding mechanism holds the cylinder member in a particular direction of rotation about the center, and the RFID chip cannot communicate with the RFID reader when the cylinder member is at a position after rotation to a predetermined angle from the particular direction.

2. The chemical liquid injection system according to claim 1, wherein the RFID chip includes a circuit chip and a chip antenna in a predetermined plane shape connected to the circuit chip,
the RFID reader includes a communication circuit and a reader antenna in a predetermined plane shape connected to the communication circuit, and
the reader antenna is put on the chemical liquid injector such that the plane directions of the reader antenna and the chip antenna are substantially in parallel with each other when the cylinder holding mechanism holds the cylinder member in the predetermined direction.

3. The chemical liquid injection system according to claim 1, wherein the RFID chip includes a circuit chip and a chip antenna in a predetermined elongated shape connected to the circuit chip,
the RFID chip is put on the liquid syringe such that the chip antenna is wound on the outer circumference of the cylinder member,
the RFID reader includes a communication circuit and a reader antenna in a predetermined elongated shape connected to the communication circuit, and the reader antenna is put on the chemical liquid injector such that the longitudinal directions of the reader antenna and the chip antenna are substantially in parallel with each other when the cylinder holding mechanism holds the cylinder member in the predetermined direction.

4. The chemical liquid injection system according to claim 2, wherein the cylinder holding mechanism includes a pair of metallic flange holding members for individually holding the left and right of the cylinder flange of the liquid syringe put from above, the RFID chip is put on the liquid syringe such that the center of the RFID chip is substantially located at the top or bottom of the cylinder member held by the cylinder holding mechanism in the predetermined direction, and the reader antenna is located below the cylinder holding mechanism.

5. The chemical liquid injection system according to claim 2, wherein the cylinder holding mechanism includes a pair of metallic flange holding members for individually holding the left and right of the cylinder flange of the liquid syringe put from above, the RFID chip is put on the liquid syringe such that the center of the RFID chip is substantially located at the top or bottom of the cylinder member held by the cylinder holding mechanism in the predetermined direction, and the reader antenna is located at a position apart from, in the forward or rearward direction, a position immediately below the RFID chip of the liquid syringe held by the cylinder holding mechanism, and the RFID reader further includes an auxiliary antenna formed of a conductor in a plane shape smaller than the reader antenna, the auxiliary antenna being located immediately below the RFID chip of the liquid syringe held by the cylinder holding mechanism and being placed substantially in parallel with the reader antenna.

6. The chemical liquid injection system according to claim 3, wherein the cylinder holding mechanism includes a pair of metallic flange holding members for individually holding the left and right of the cylinder flange of the liquid syringe put from above, the RFID chip is put on the liquid syringe such that the center of the RFID chip is substantially located at the top or bottom of the cylinder member held by the cylinder holding mechanism in the predetermined direction, and the reader antenna is located at a position apart from, in the forward or reared direction, a position immediately below the RFID chip of the liquid syringe held by the cylinder holding mechanism, and the RFID reader further includes an auxiliary antenna formed of a conductor in a predetermined elongated shape shorter and smaller than the reader antenna, the auxiliary antenna being located immediately below the RFID chip of the liquid syringe held by the cylinder holding mechanism and being placed substantially in parallel with the reader antenna.

7. The chemical liquid injection system according to claim 1, wherein a leading end of the piston member is located at the trailing end of the cylinder member in the liquid syringe, and the RFID chip is put on an outer circumference of the trailing end of the cylinder member at a position overlapping the leading end of the piston member.

8. The chemical liquid injection system according to claim 1, wherein the RFID chip has various types of data recorded thereon as the recorded data, and the chemical liquid injector includes data display means for outputting as display at least some of the various types of data wirelessly received from the RFID chip.

9. The chemical liquid injection system according to claim 1, wherein the computer unit is further configured to return the piston driving mechanism to an initial position when completion of injection operation is detected and then detection of the RFID chip by the RFID reader is ended.

10. The chemical liquid injection system according to claim 1, wherein the computer unit is further configured to hold the various types of data wirelessly received from the RFID chip and injection control means for controlling to control operation of the piston driving mechanism in accordance with at least some of the held various types of data.

11. The chemical liquid injection system according to claim 10, wherein the liquid syringe is of a pre-filled type which is shipped with the liquid syringe filled with a contrast medium as the liquid to be injected into a patient whose diagnostic image is taken by an imaging diagnostic apparatus, and the RFID chip of the liquid syringe has a variable pattern set thereon for changing an injection rate of the contrast medium over time, and the computer unit changes an operation rate of the piston driving mechanism over time in accordance with the variable pattern.

12. The chemical liquid injection system according to claim 1, wherein the computer unit is further configured to store a predetermined check condition as data, compare the stored check condition with the various types of data wirelessly received from the RFID chip, and output and notify a check alarm in accordance with the comparison result.

13. The chemical liquid injection system according to claim 1, wherein the RFID chip has at least a production number of the liquid syringe for each item set thereon, and the computer unit is further configured to store data of the production number of the liquid syringe mounted and used to perform injection operation, compare the stored production number with a new production number, and output and notify a check alarm when the compared production numbers match.

14. The chemical liquid injection system according to claim 1, wherein the RFID chip is put on the liquid syringe to record at least the fact that that liquid syringe is once used, and the computer unit is further configured to record, data of the fact that that liquid syringe has been mounted and the liquid thereof has been injected on the RFID chip of the liquid syringe, and output and notify a check alarm when that data is wirelessly received from the RFID chip of the liquid syringe.

15. A chemical liquid injector used in a chemical liquid injection system, said chemical liquid injector adapted to inject the liquid into a patient by moving a cylinder member relative to a piston member of a liquid syringe, said injector comprising: a cylinder holding mechanism for holding the cylinder member; a piston driving mechanism for at least pressing the piston member into the held cylinder member; an RFID reader for wirelessly receiving the recorded data from an RFID chip mounted on the liquid syringe at a predetermined position of the cylinder member for wirelessly transmitting recorded data; and a computer unit configured to allow operation of the piston driving mechanism only when the recorded data is wirelessly received, wherein the RFID reader continuously detects the RFID chip during injection and if said detection is interrupted, injection operation by the piston driving mechanism is stopped, and the RFID chip can communicate with the RFID reader when the cylinder holding mechanism holds the cylinder member in the particular direction, and the RFID chip cannot communicate with the RFID reader when the cylinder member is at a position after rotation to a predetermined angle from the particular direction.

16. A liquid syringe of used in a chemical liquid injection system, comprising: a cylindrical cylinder member and a piston member slidably inserted into the cylinder member from the back thereof;

the cylinder member including an annular cylinder flange formed on an outer circumference of a trailing end; an RFID chip for wirelessly receiving recorded data put on the cylinder member at a predetermined position, and an RFID reader, wherein the RFID reader continuously detects the RFID chip during injection, and if said detection is interrupted, injection operation by the piston driving mechanism is stopped, the RFID chip can communicate with the RFID reader when the cylinder holding mechanism holds the cylinder member in the particular direction, and the RFID chip cannot communicate with the RFID reader when the cylinder member is at a position after rotation to a predetermined angle from the particular direction.

17. A chemical liquid injection system comprising:

a cylindrical cylinder member and a piston member slidably inserted into the cylinder member;

an RFID chip fixedly disposed with respect to the cylinder member;

a cylinder holding mechanism for holding the cylinder member at a predetermined position of the cylinder member;

a piston driving mechanism for pressing the piston member into the cylinder member when being held by the cylinder holding mechanism for injecting a liquid into a subject; and an RFID reader fixedly disposed with respect to the cylinder holding mechanism, wherein the RFID reader can wirelessly communicate with the RFID chip when the cylinder holding mechanism holds the cylinder member at the predetermined position and cannot communicate with the RFID chip when the cylinder holding mechanism does not hold the cylinder member at a position of the cylinder member away from the predetermined position, and the RFID reader continuously detects the RFID chip during injection, and if said detection is interrupted, injection operation by the piston driving mechanism is stopped.

18. The chemical liquid injection system according to claim 17, wherein the predetermined position of the cylinder member when being held by the cylinder holding mechanism is a predetermined rotational angle of the cylinder member about its axis.

19. The chemical liquid injection system according to claim 17, further comprising an operation controller for driving the piston driving mechanism only when the cylinder member is held by the cylinder holding mechanism.

20. The chemical liquid injection system according to claim 17, wherein the RFID chip wirelessly transmits recorded data to the RFID reader when the RFID reader communicates with the RFID chip.

* * * * *

UNITED STATES PATENT AND TRADEMARK OFFICE
CERTIFICATE OF CORRECTION

| | |
|---|---|
| PATENT NO. | : 7,686,789 B2 |
| APPLICATION NO. | : 11/572091 |
| DATED | : March 30, 2010 |
| INVENTOR(S) | : Shigeru Nemoto, Seiichi Ono and Masahiro Sakakibara |

It is certified that error appears in the above-identified patent and that said Letters Patent is hereby corrected as shown below:

Sheet 5 of 14 (Fig. 5), Numeral 104; Change "LIOUID" to --LIQUID--.

Column 2, line 34; Change "None-patent" to --Non-patent--.

Column 2, line 36; After "2004)" insert --.--.

Column 3, line 14; Change "Chemical" to --chemical--.

Column 4, line 37; Change "right" to --right,--.

Column 6, line 49; Change "I-chip" to --µ-chip--.

Column 18, line 23; In Claim 1, change "therof" to --thereof,--.

Column 19, line 45; In Claim 6, change "reared" to --rearward--.

Column 20, line 66; In Claim 16, after "syringe" delete "of".

Signed and Sealed this

Twelfth Day of October, 2010

David J. Kappos
*Director of the United States Patent and Trademark Office*